(12) United States Patent
Flaherty et al.

(10) Patent No.: US 8,812,096 B2
(45) Date of Patent: Aug. 19, 2014

(54) BIOLOGICAL INTERFACE SYSTEM WITH PATIENT TRAINING APPARATUS

(75) Inventors: J. Christopher Flaherty, Topsfield, MA (US); Abraham H. Caplan, Cambridge, MA (US)

(73) Assignee: BrainGate Co., LLC, Ponte Vedra Beach, FL (US)

( * ) Notice: Subject to any disclaimer, the term of this patent is extended or adjusted under 35 U.S.C. 154(b) by 2411 days.

(21) Appl. No.: 11/320,710

(22) Filed: Dec. 30, 2005

(65) Prior Publication Data

US 2006/0167371 A1 Jul. 27, 2006

Related U.S. Application Data

(60) Provisional application No. 60/643,358, filed on Jan. 10, 2005.

(51) Int. Cl.
| | |
|---|---|
| *A61B 5/04* | (2006.01) |
| *G06F 3/01* | (2006.01) |
| *A61F 2/50* | (2006.01) |
| *A61F 2/68* | (2006.01) |
| *G09B 23/28* | (2006.01) |
| *G06N 3/06* | (2006.01) |
| *G09B 19/00* | (2006.01) |
| *A61F 2/76* | (2006.01) |
| *A61F 2/70* | (2006.01) |

(52) U.S. Cl.
CPC . *G06F 3/015* (2013.01); *A61F 2/50* (2013.01); *A61F 2/68* (2013.01); *G09B 23/28* (2013.01); *A61F 2002/7615* (2013.01); *A61F 2002/704* (2013.01); *G06N 3/061* (2013.01); *G09B 19/00* (2013.01)
USPC .......................................... 600/544

(58) Field of Classification Search
USPC .................. 600/544, 545; 623/25; 463/36
See application file for complete search history.

(56) References Cited

U.S. PATENT DOCUMENTS 3,837,339 A    9/1974   Aisenberg et al.
(Continued)

FOREIGN PATENT DOCUMENTS

EP    0 911 061 A    4/1999
(Continued)

OTHER PUBLICATIONS

Kensall D. Wise et al., "An Integrated-Circuit Approach to Extraceullar Microelectrodes," IEEE Transactions on Biomedical Engineering, vol. BME-17, No. 3, Jul. 1970, pp. 238-247.

(Continued)

*Primary Examiner* — Michael D'Angelo
*Assistant Examiner* — Christian Jang
(74) *Attorney, Agent, or Firm* — SoCal IP Law Group LLP; M. Kala Sarvaiya; Steven C. Sereboff

(57) ABSTRACT

Various embodiments of a biological interface system and related methods are disclosed. The system may include a sensor having a plurality of electrodes for detecting multicellular signals emanating from one or more living cells of a patient, and a processing unit configured to receive the multicellular signals from the sensor and process the multicellular signals to produce a processed signal. The processing unit may be configured to transmit the processed signal to a controlled device that is configured to receive the processed signal. The system may also include a patient training apparatus configured to receive a patient training signal that causes the patient training apparatus to controllably move one or more joints of the patient. The system may be configured to perform an integrated patient training routine to produce the patient training signal, to store a set of multicellular signal data detected during a movement of the one or more joints, and to correlate the set of multicellular signal data to a second set of data related to the movement of the one or more joints.

112 Claims, 6 Drawing Sheets

(56) References Cited

U.S. PATENT DOCUMENTS

| | | | |
|---|---|---|---|
| 3,850,161 A | 11/1974 | Liss | |
| 4,055,175 A | 10/1977 | Clemens et al. | |
| 4,146,029 A | 3/1979 | Ellinwood, Jr. | |
| 4,294,245 A | 10/1981 | Bussey | |
| 4,360,031 A | 11/1982 | White | |
| 4,461,304 A | 7/1984 | Kuperstein | |
| 4,566,464 A | 1/1986 | Piccone et al. | |
| 4,633,889 A | 1/1987 | Talalla et al. | |
| 4,690,142 A | 9/1987 | Ross et al. | |
| 4,837,049 A | 6/1989 | Byers et al. | |
| 4,865,048 A | 9/1989 | Eckerson | |
| 4,878,913 A | 11/1989 | Aebischer et al. | |
| 4,883,666 A | 11/1989 | Sabel et al. | |
| 4,969,468 A | 11/1990 | Byers et al. | |
| 5,037,376 A | 8/1991 | Richmond et al. | |
| 5,081,990 A | 1/1992 | Deletis | |
| 5,092,329 A | 3/1992 | Graupe et al. | |
| 5,119,832 A | 6/1992 | Xavier | |
| 5,156,844 A | 10/1992 | Aebischer et al. | |
| 5,215,088 A | 6/1993 | Normann et al. | |
| 5,325,862 A | 7/1994 | Lewis et al. | |
| 5,325,865 A | 7/1994 | Beckman et al. | |
| 5,361,760 A | 11/1994 | Normann et al. | |
| 5,423,877 A | 6/1995 | Mackey | |
| 5,445,608 A | 8/1995 | Chen et al. | |
| 5,458,631 A | 10/1995 | Xavier | |
| 5,474,547 A | 12/1995 | Aebischer et al. | |
| 5,476,441 A | 12/1995 | Durfee et al. | |
| 5,549,656 A | 8/1996 | Reiss | |
| 5,617,871 A | 4/1997 | Burrows | |
| 5,622,170 A | 4/1997 | Schulz | |
| 5,638,826 A | 6/1997 | Wolpaw et al. | |
| 5,687,291 A | 11/1997 | Smyth | |
| 5,692,517 A | 12/1997 | Junker | |
| 5,697,951 A | 12/1997 | Harpstead et al. | |
| 5,702,432 A | 12/1997 | Chen et al. | |
| 5,713,923 A | 2/1998 | Ward et al. | |
| 5,724,987 A | 3/1998 | Gevins et al. | |
| 5,735,885 A | 4/1998 | Howard, III et al. | |
| 5,758,651 A | 6/1998 | Nygard et al. | |
| 5,797,898 A | 8/1998 | Santini, Jr. et al. | |
| 5,814,089 A | 9/1998 | Stokes et al. | |
| 5,843,093 A | 12/1998 | Howard, III | |
| 5,843,142 A | 12/1998 | Sultan | |
| 5,855,801 A | 1/1999 | Lin et al. | |
| 5,857,978 A | 1/1999 | Hively et al. | |
| 5,873,840 A | 2/1999 | Neff | |
| 5,928,228 A | 7/1999 | Kordis et al. | |
| 5,938,688 A | 8/1999 | Schiff | |
| 5,938,689 A | 8/1999 | Fischell et al. | |
| 5,938,690 A | 8/1999 | Law et al. | |
| 5,995,868 A | 11/1999 | Dorfmeister et al. | |
| 6,001,065 A | 12/1999 | DeVito | |
| 6,006,124 A | 12/1999 | Fischell et al. | |
| 6,016,449 A | 1/2000 | Fischell et al. | |
| 6,018,682 A | 1/2000 | Rise et al. | |
| 6,024,700 A | 2/2000 | Nemirovski et al. | |
| 6,024,702 A | 2/2000 | Iversen | |
| 6,027,456 A | 2/2000 | Feler et al. | |
| 6,038,477 A | 3/2000 | Kayyali | |
| 6,044,292 A | 3/2000 | Heyrend et al. | |
| 6,061,593 A | 5/2000 | Fischell et al. | |
| 6,086,582 A | 7/2000 | Altman et al. | |
| 6,091,015 A | 7/2000 | del Valle et al. | |
| 6,092,058 A | 7/2000 | Smyth | |
| 6,094,598 A | 7/2000 | Elsberry et al. | |
| 6,113,553 A | 9/2000 | Chubbuck | |
| 6,125,300 A | 9/2000 | Weijand et al. | |
| 6,128,538 A | 10/2000 | Fischell et al. | |
| 6,134,474 A | 10/2000 | Fischell et al. | |
| 6,144,875 A | 11/2000 | Schweikard et al. | |
| 6,154,678 A | 11/2000 | Lauro | |
| 6,161,045 A | 12/2000 | Fischell et al. | |
| 6,163,725 A | 12/2000 | Peckham et al. | |
| 6,169,981 B1 | 1/2001 | Werbos | |
| 6,171,239 B1 | 1/2001 | Humphrey | |
| 6,175,762 B1 | 1/2001 | Kirkup et al. | |
| 6,181,965 B1 | 1/2001 | Loeb et al. | |
| 6,185,455 B1 | 2/2001 | Loeb et al. | |
| 6,216,045 B1 | 4/2001 | Black et al. | |
| 6,224,549 B1 | 5/2001 | Drongelen | |
| 6,240,315 B1 | 5/2001 | Mo et al. | |
| 6,254,536 B1 | 7/2001 | DeVito | |
| 6,263,237 B1 | 7/2001 | Rise | |
| 6,280,394 B1 | 8/2001 | Maloney et al. | |
| 6,304,775 B1 | 10/2001 | Iasemidis et al. | |
| 6,309,410 B1 | 10/2001 | Kuzma et al. | |
| 6,313,093 B1 | 11/2001 | Frey, II | |
| 6,319,241 B1 | 11/2001 | King et al. | |
| 6,353,754 B1 | 3/2002 | Fischell et al. | |
| 6,354,299 B1 | 3/2002 | Fischell et al. | |
| 6,356,784 B1 | 3/2002 | Lozano et al. | |
| 6,358,202 B1 | 3/2002 | Arent | |
| 6,360,122 B1 | 3/2002 | Fischell et al. | |
| 6,366,813 B1 | 4/2002 | DiLorenzo | |
| 6,416,520 B1 | 7/2002 | Kynast et al. | |
| 6,427,086 B1 | 7/2002 | Fischell et al. | |
| 6,436,708 B1 | 8/2002 | Leone et al. | |
| 6,459,936 B2 | 10/2002 | Fischell et al. | |
| 6,466,822 B1 | 10/2002 | Pless | |
| 6,473,639 B1 | 10/2002 | Fischell et al. | |
| 6,480,743 B1 | 11/2002 | Kirkpatrick et al. | |
| 6,549,804 B1 | 4/2003 | Osorio et al. | |
| 6,577,893 B1 | 6/2003 | Besson et al. | |
| 6,620,415 B2 | 9/2003 | Donovan | |
| 6,658,287 B1 | 12/2003 | Litt et al. | |
| 7,010,351 B2 | 3/2006 | Firlik et al. | |
| 7,162,305 B2 | 1/2007 | Tong et al. | |
| 7,212,851 B2 | 5/2007 | Donoghue et al. | |
| 7,280,870 B2 | 10/2007 | Nurmikko et al. | |
| 7,346,396 B2 | 3/2008 | Barriskill et al. | |
| 7,381,192 B2 | 6/2008 | Brodard et al. | |
| 7,392,079 B2 | 6/2008 | Donoghue et al. | |
| 7,647,097 B2 | 1/2010 | Flaherty et al. | |
| 7,751,877 B2 | 7/2010 | Flaherty et al. | |
| 2001/0023368 A1 | 9/2001 | Black et al. | |
| 2001/0027336 A1 | 10/2001 | Gielen et al. | |
| 2001/0028309 A1 | 10/2001 | Torch | |
| 2001/0029391 A1 | 10/2001 | Gluckman et al. | |
| 2001/0051819 A1 | 12/2001 | Fischell et al. | |
| 2001/0056290 A1 | 12/2001 | Fischell et al. | |
| 2002/0002390 A1 | 1/2002 | Fischell et al. | |
| 2002/0013612 A1 | 1/2002 | Whitehurst | |
| 2002/0016638 A1 | 2/2002 | Mitra et al. | |
| 2002/0077534 A1 | 6/2002 | DuRousseau | |
| 2002/0077620 A1 | 6/2002 | Sweeney et al. | |
| 2002/0082514 A1 | 6/2002 | Williams et al. | |
| 2002/0099412 A1 | 7/2002 | Fischell et al. | |
| 2002/0169485 A1 | 11/2002 | Pless et al. | |
| 2003/0004428 A1 | 1/2003 | Pless et al. | |
| 2003/0050569 A1* | 3/2003 | Shenoy et al. | 600/544 |
| 2003/0074032 A1 | 4/2003 | Gliner | |
| 2003/0082507 A1 | 5/2003 | Stypulkowski | |
| 2003/0083716 A1 | 5/2003 | Nicolelis et al. | |
| 2003/0083724 A1 | 5/2003 | Jog et al. | |
| 2003/0093129 A1 | 5/2003 | Nicolelis et al. | |
| 2003/0139782 A1 | 7/2003 | Duncan et al. | |
| 2003/0139783 A1* | 7/2003 | Kilgore et al. | 607/49 |
| 2004/0006264 A1 | 1/2004 | Mojarradi et al. | |
| 2004/0073414 A1 | 4/2004 | Bienenstock et al. | |
| 2004/0138579 A1 | 7/2004 | Deadwyler et al. | |
| 2004/0267320 A1 | 12/2004 | Taylor et al. | |
| 2005/0090756 A1 | 4/2005 | Wolf et al. | |
| 2005/0137652 A1 | 6/2005 | Cauller et al. | |
| 2005/0182341 A1* | 8/2005 | Katayama et al. | 600/587 |
| 2005/0273890 A1 | 12/2005 | Flaherty et al. | |
| 2006/0049957 A1 | 3/2006 | Surgenor et al. | |
| 2006/0058627 A1 | 3/2006 | Flaherty et al. | |
| 2006/0149338 A1 | 7/2006 | Flaherty et al. | |
| 2006/0167371 A1 | 7/2006 | Flaherty et al. | |
| 2006/0167530 A1 | 7/2006 | Flaherty et al. | |
| 2006/0167564 A1 | 7/2006 | Flaherty et al. | |
| 2006/0173259 A1 | 8/2006 | Flaherty et al. | |
| 2006/0189900 A1 | 8/2006 | Flaherty | |

(56) References Cited

U.S. PATENT DOCUMENTS

| | | | |
|---|---|---|---|
| 2006/0195042 | A1 | 8/2006 | Flaherty |
| 2006/0206167 | A1 | 9/2006 | Flaherty et al. |
| 2006/0241356 | A1 | 10/2006 | Flaherty |
| 2006/0253166 | A1 | 11/2006 | Flaherty et al. |
| 2007/0032738 | A1 | 2/2007 | Flaherty et al. |
| 2007/0156126 | A1 | 7/2007 | Flaherty |
| 2008/0064966 | A1 | 3/2008 | Brockway et al. |
| 2010/0023021 | A1 | 1/2010 | Flaherty |
| 2010/0063411 | A1 | 3/2010 | Donoghue et al. |

FOREIGN PATENT DOCUMENTS

| | | |
|---|---|---|
| WO | WO 01/43635 | 6/2001 |
| WO | WO 01/60445 | 8/2001 |
| WO | WO 01/78833 | 10/2001 |
| WO | WO 01/93756 A2 | 12/2001 |
| WO | WO 02/093312 A2 | 11/2002 |
| WO | WO 02/100267 A1 | 12/2002 |
| WO | WO 03/035165 | 5/2003 |
| WO | WO 03/037231 | 5/2003 |
| WO | WO 03/061465 A2 | 7/2003 |
| WO | WO 2006/044793 A2 | 4/2006 |

OTHER PUBLICATIONS

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp. 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B-Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minessota Epilepsy Group of United and St. Paul Children's Hospital; and Human Motor Control Section, National Institute of Neurological Disorders and Stroke, National Institutes of Health, Electroencephalorophy and Clinical Neurophysiology, No. 93, 1994, pp. 390-403.

Anthony L. Owens et al., "Multi-electrode array for measuring evoked potentials from surface of ferret primary auditory cortex," Jounal of Neuroscience Methods, vol. 58, Nos. ½, May 1995, pp. 209-220.

Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D.M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp. 237-278.

Qing Bai et al., "A High-Yield Process for Three-Dimensional Microelectrode Arrays," Solid-State Sensor and Actuator Workshop, Hilton Head, South Carolina, Jun. 2-6, 1996, pp. 262-265.

Apostolos P. Georgopoulos et al., "Neuronal Population Coding of Movement Direction," Science, vol. 233, Sep. 26, 1986, pp. 1416-1419.

Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp. 719-732.

Patrick K. Campbell et al., "A chronic intracortical electrode array: Preliminary results," Journal of Biomed. Material Res.: Applied Biomaterials, vol. 23, No. 2, 1989, pp. 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al., "A Glass/Silicon Composite Intracortical Electrode Array," Annals of Biomedical Engineering. vol. 20, 1992, pp. 423-437.

Miguel A. L. Nicolelis et al., "Induction of immediate spatiotemporal changes in thalamic networks by peripheral block of ascending cutaneous information," Letters to Nature, vol. 361, Feb. 11, 1993, pp. 533-536.

Reinhard Eckhorn et al., "A new method for the insertion of multiple microprobes into neural and muscular tissue, including fiber electrodes, fine wires, needles and microsensors," Journal of Neuroscience Methods, vol. 49, Nos. 1/2, 1993, pp. 175-179.

Craig T. Nordhausen et al., "Optimizing recording capabilities of the Utah Intracortical Electrode Array," Brain Research, vol. 637, Nos. 1/2 , Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Miguel A. L. Nicolelis et al., "Spatiotemporal Structure of Somatosensory Responses of Many-Neuron Ensembles in the Rat Ventral PosteriorMedial Nucleus of the Thalamus," The Journal of Neuroscience, vol. 14, No. 6, Jun. 1994, pp. 3511-3532.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.

P. Nisbet, "intergrating assistive technologies: current practices and future possibilities," Med. Eng. Phys., vol. 18, No. 3, 1996, pp. 193-202.

(56) References Cited

OTHER PUBLICATIONS

Miguel A. L. Nicolelis et al., "Reconstructing the Engram: Simultaneous, Multisite, Many Sinle Neuron Recordings," Nueron, vol. 18, Apr. 1997, pp. 529-537.
TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.
Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.
Nicolelis, Miguel A.L., "Trigeminal System Plasticity During Facial Anethesia," Department of Health and Human Services, Public Health Service, Grant No. 2 R01 DE11451-05, Including Summary Statement, Oct. 1997.
Robert M. Bradley et al., "Long term chronic recordings from peripheral sensory fibers using a sieve electrode array," Journal of Neuroscience Methods, vol. 73, 1997, pp. 177-186.
David K. Warland et al., "Decoding Visual Information From a Population of Retinal Ganglion Cells," The American Physiological Society, 1997, pp. 2336-2350.
Steven P. Wise et al., "Premotor and Parietal Cortex: Cortiococortical Connectivity and Combinatorial Computations," Annual Review of Neuroscience, vol. 20, 1997, pp. 25-42.
P.R. Kennedy et al., "Restoration of neural output from a paralyzed patient by a direct brain connection," NeuroReport, vol. 9, No. 8, Jun. 1998 pp. 1707-1711.
Paolo Dario et al., "Neural Interfaces for Regenerated Nerve Stimulation and Recording," IEEE Transactions on Rehabilitation Engineering, vol. 6, No. 4, Dec. 1998, pp. 353-363.
Nicholas G. Hatsopoulos et al., "Information about movement direction obtained from synchronous activity of motor cortical neurons," Proc. Natl. Acad. Sci. USA, vol. 95, Dec. 1998, pp. 15706-15711.
John P. Donoghue et al., "Neural Discharge and Local Field Potential Oscillations in Primate Motor Cortex During Voluntary Movements," The American Physiological Society, 1998, pp. 159-173.
Nicolelis, Miguel A.L., "Trigeminal System Plasticity During Facial Anethesia," Department of Health and Human Services, Public Health Service, Grant No. 2 R01 DE11451-06, Apr. 1999.
Gregor Rainer et al., "Prospective Coding for Objects in Primate Prefrontal Cortex," The Journal of Neuroscience, vol. 19, No. 13, Jul. 1, 1999, pp. 5493-5505.
John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, pp. 664-670.
E. M. Maynard et al, "Neuronal Interactions Improve Cortical Population Coding of Movement Direction," The journal of Neuroscience, vol. 19, No. 18, Sep. 15, 1999, pp. 8083-8093.
F. Gandolfo et al., "Cortical correlates of learning in monkeys adapting to a new dynamical environment," PNAS, vol. 97, No. 5, Feb. 29, 2000, pp. 2259-2263.
J. F. Marsden et al., "Organization of Cortical Activities Related to Movement in humans," The Journal of Neuroscience, vol. 20, No. 6, Mar. 15, 2000, pp. 2307-2314.
D. Gareth Evans et al., "Controlling mouse Pointer Position Using an Infrared Head-Operated Joystick," IEEE Transaction on Rehabilitation Engineering, vol. 8, No. 1, Mar. 2000, pp. 107-117.
Qing Bai et al., "A High-Yield Microassembly Structure for Three-Dimensional Microelectrode Arrays," IEEE Transactions on Biomedical Engineering, vol. 47, No. 3, Mar. 2000, pp. 281-289.
Nicolelis, Miguel A.L., "Trigeminal System Plasticity During Facial Anethesia," Department of Health and Human Services, Public health Service, Grant No. 2 R01 DE11451-07, Apr. 2000.
Nicolelis, Miguel A.L., "Corticofugal Modulation of Tactile Sensory Processing," Department of Health and Human Services, Public Health Service, National Institute of Dental and Craniofacial Research of the Nationsl Institutes of health, Grant No. 1 R01 DE013810-01 A1, Jun. 2000.
Jonathan R. Wolpaw et al., "Brain-Computer Interface Technology: A Review of the First International Meeting," IEEE Transactions on Rehabilitation Engineering, vol. 8, No. 2, Jun. 2000, pp. 164-173.
Simon P. Levine et al., "A Direct Brain Interface Based on Event-Related potentials," IEEE Transactions on Rehabilitation Engineering, vol. 8, No. 2, Jun. 2000, pp. 180-185.
Robert E. Isaacs et al., "Work Toward Real-Time Control of a cortical Neural Prothesis," IEEE Transactions on Rehabilitation Engineering, vol. 8, No. 2, Jun. 2000, pp. 196-198.
Scott Makeig et al., A Natural Basis for Efficient Brain-Actuated Control, IEEE Transactions on Rehabilitation Engineering, vol. 8, No. 2, Jun. 2000, pp. 208-211.
Johan Wessberg et al., "Real-time prediction of hand trajectory by ensembles of cortical neurons in primates," Nature, vol. 408, Nov. 16, 2000, pp. 361-365.
Jerome N. Sanes et al., "Plasticity and Primary Motor Cortex," Annual Reviews, Neuroscience, Brown University, Library, vol. 23, 2000, pp. 393-415.
Jonathan C. Jarvis et al., "The application and technology of implantable neuromuscular stimulators: an introduction and overview," Medical Engineering & Physics, No. 23, Jan. 11, 2001, pp. 3-7.
Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.
Gerald E. Loeb et al., "BION™ system for distributed neural prosthetic interfaces," Medical Engineering & Physics, vol. 23, Jan. 26, 2001, pp. 9-18.
Patrick J. Rousche et al., "Flexible Polyimide-Based Intracortical Electrode Arrays with Bioactive Capability," IEEE Transactions on Biomedical Engineering, vol. 48, No. 3, Mar. 2001, pp. 361-371.
Nicolelis, Miguel A.L., "Trigeminal System Plasticity During Facial Anethesia," Department of Health and Human Services, Public Health Service, Grant No. 2 R01 DE11451-08, Apr. 2001.
Qing Bai et al., "Single-Unit Neural Recording with Active Microelectrode Arrays," IEEE Transactions on Biomedical Engineering, vol. 48, No. 8, Aug. 2001, pp. 911-920.
David L. Zealear et al., "The Biocompatibility, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.
Dawn M. Taylor et al., "Using Virtual Reality to Test the Feasibility of Controlling an Upper Limb Fes System Directly from Multiunit Activity in the Motor Cortex," Arizona State University; and the Neurosciences Institute, Summer 2001, pp. 1-3.
Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.
Shay Shoham, "Advances Towards an Implantable Motor Cortical Interface," The University of Utah, Dec. 2001, pp. 1-157.
John K. Chapin et al., "Neural Prostheses for Restoration of Sensory and Motor Function," CRC Press, LLC, 2001, Chapters 6, 8 and 9 pp. 179-219, pp. 235-261, pp. 263-283.
Andrew B. Schwartz et al., "Extraction algorithms for cortical control of arm prosthetics," The Neuroscience Institute; and Department of Bioengineering, Arizona State University, 2001, pp. 701-707.
István Ulbert et al., "Multiple microelectrode-recording system for human intracortical applications," Journal of Neuroscience Methods, vol. 106, 2001, pp. 69-79.
Mijail D. Serruya et al., "Instant Neural Control of a Movement Signal," Nature, vol. 416, Mar. 14, 2002, pp. 141-142.
Nicolelis, Miguel A.L., "Corticofugal Modulation of Tactile Sensory Processing," Department of Health and Human Services, Public health Service, National Institute of Dental and Craniofacial Research of the Nationsl Institutes of Health, Grant No. 5 R01 DE013810-02, Mar. 2002.

(56) References Cited

OTHER PUBLICATIONS

Nicolelis, Miguel A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7, 2002, pp. 1829-1832.

John P. Donoghue, "Connecting cortex to machines: recent advances in brain interfaces," Nature Neuroscience Supplement, vol. 5, Nov. 2002, pp. 1085-1088.

Y. Gao, et al., "Probabilistic Inference of Hand Motion from Neural Activity in Motor Cortex," In Advances in Neural Information Processing Systems 14, The MIT Press, 2002, pp. 1-8.

Mijail Serruya et al., "Robustness of neuroprosthetic decoding algorithms," Biological Cybernetics, 2003, pp. 1-10.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter,"Brown University, Providence, RI, Jul. 1, 2003, pp. 1-30.

Jose M. Camiena et al., "Learning to Control a Brain-Machine Interface for Reaching and Grasping by Primates," PLOS Biology, vol. 1, Issue 2, Oct. 13, 2003, pp. 1-16.

Nicolelis, Miguel A.L., "Brain-machine Interfaces to Restore Motor Function and Probe Neural Circuits," Nature Reviews, Neuroscience, vol. 4, May 2003, pp. 417-422.

Libet, Benjamin, "Unconscious Cerebral Initiative and the Role of Conscious Will in Voluntary Action," The Behavioral and Brain Sciences 1995) 8, pp. 529-566.

Norretranders, Tor, "The User Illusion," Penguin Books, 1991, Chapter 12, pp. 310-328.

Mohammad Mojarradi, "A Miniaturized Neuroprosthesis Suitable for Implantation Into the Brain," IEEE Transactions on Neural Systems and Rehabilitation Engineering, vol. 11, No. 1, Mar. 2003.

Morten K. Haugland et al., "Cutaneous Whole Nerve Recordings Used for Correction of Footdrop in Hemiplegic Man," IEEE Transactions on Neural Systems and Rehabilitation Engineering, vol. 3, No. 4, Dec. 1995.

Ferdinando Mussa-Ivaldi et al., "Brain-machine interfaces: computational demands and clinical needs meet basic neuroscience," TRENDS in Neurosciences, vol. 26, No. 6, Jun. 2003, pp. 329-334.

D.N. Harvey et al., "Multiple-Output Electromyographic Switching System," 1978 ISA, Pittsburgh, PA, 1978, pp. 121-123.

Faisal Karmali et al.," Environmental Control by a Brain-Computer Interface," Proceedings of the $22^{nd}$ Annual Embs Ind Conf., Jul. 23-28, 2000, Chicago, IL, pp. 2990-2992.

Alex Mihailidis et al. "Using artificial intelligence to assist people with dementia to be more independent," Proceedings of the $22^{nd}$ Annual Embs Int'l Conf., Jul. 23-28, 2000, Chicago, IL, pp. 2993-2996.

Touradj Ebrahimi et al., Brain-computer Interface in Multimedia Communication, IEEE Signal Processing Magazine, vol. 20, No. 1, Jan. 2003, pp. 14-24.

Gernot R. Muller et al., Implementation of a Telemonitoring System for the Control of an EEG-Based Brain Computer Interface, IEEE Transactions on Neural Systems and Rehabilitation Engineering, vol. 11, No. 1, Mar. 2002, pp. 54-59.

\* cited by examiner

BIOLOGICAL INTERFACE SYSTEM WITH PATIENT TRAINING APPARATUS

This application claims the benefit of priority under 35 U.S.C. §119(e) of U.S. Provisional Application No. 60/643,358, filed Jan. 10, 2005. This application relates to commonly assigned U.S. application Ser. No. 11/320,711 of J. Christopher Flaherty et al., entitled "BIOLOGICAL INTERFACE SYSTEM WITH SURROGATE CONTROLLED DEVICE" and filed on the same date as the present application. The complete subject matter of the above-referenced applications is incorporated by reference herein.

FIELD OF THE INVENTION

The present invention relates to medical devices and related methods. More particularly, various embodiments relate to biological interface systems that include one or more devices controlled by processed multicellular signal of a patient. A processing unit produces a control signal based on multicellular signals received from a sensor comprising multiple electrodes. The system may include a patient training apparatus that is utilized to configure the system to optimize control of the device.

DESCRIPTION OF RELATED ART

Biological interface devices, for example neural interface devices, are currently under development for numerous patient applications including restoration of lost function due to traumatic injury or neurological disease. Sensors, such as electrode arrays, implanted in the higher brain regions that control voluntary movement, can be activated voluntarily to generate electrical signals that can be processed by a biological interface device to create a thought invoked control signal. Such control signals can be used to control numerous devices including computers and communication devices, external prostheses, such as an artificial arm or functional electrical stimulation of paralyzed muscles, as well as robots and other remote control devices. Patients afflicted with amyotrophic lateral sclerosis (Lou Gehrig's Disease), particularly those in advanced stages of the disease, would also be appropriate for receiving a neural interface device, even if just to improve communication to the external world, including Internet access, and thus improve their quality of life.

Early attempts to utilize signals directly from neurons to control an external prosthesis encountered a number of technical difficulties. The ability to identify and obtain stable electrical signals of adequate amplitude was a major issue. Another problem that has been encountered is caused by the changes that occur to the neural signals that occur over time, resulting in a degradation of system performance. Neural interface systems that utilize other neural information or other neural data, such as electrocorticogram (ECoG) signals, local field potentials (LFPs) and electroencephalogram (EEG) signals have similar issues to those associated with individual neuron signals. Since all of these signals result from the activation of large groups of neurons, the specificity and resolution of the control signal that can be obtained is limited. However, if these lower resolution signals could be properly identified and the system adapt to their changes over time, simple control signals could be generated to control rudimentary devices or work in conjunction with the higher power control signals processed directly from individual neurons.

Commercialization of these neural interfaces has been extremely limited, with the majority of advances made by universities in a preclinical research setting. As the technologies advance and mature, the natural progression will be to more sophisticated human applications, such as those types of devices regulated by various governmental regulatory agencies including the Food and Drug Administration in the United States.

As sophisticated biological interface systems are approved by the FDA and become commercially available, these systems need to include numerous safety features required for medical devices. It will also be required that the systems have simplified configuration routines, such as patient training routines, which assure reliable functionality. Convenience and flexibility to the patient, their caregivers and family members may also be desirable. There is therefore a need for an improved biological interface system which includes a sophisticated patient training routine. Automation, as well as convenience to health care providers, may provide numerous benefits to the patient and the health care system.

SUMMARY OF THE INVENTION

According to an exemplary aspect of the invention, a biological interface system may be provided. The system may comprise a sensor comprising a plurality of electrodes for detecting multicellular signals emanating from one or more living cells of a patient and a processing unit configured to receive the multicellular signals from the sensor and process the multicellular signals to produce a processed signal. The processing unit may be configured to transmit the processed signal to a controlled device that is configured to receive the processed signal. The system may also comprise a patient training apparatus configured to receive a patient training signal that causes the patient training apparatus to controllably move one or more joints of the patient. The system may be configured to perform an integrated patient training routine to produce the patient training signal, to store a set of multicellular signal data detected during a movement of the one or more joints, and to correlate the set of multicellular signal data to a second set of data related to the movement of the one or more joints.

Some exemplary aspects may provide a biological interface system comprising a sensor comprising a plurality of electrodes for detecting multicellular signals emanating from one or more living cells of a patient, a processing unit configured to receive the multicellular signals from the sensor and process the multicellular signals to produce a processed signal, the processing unit being configured to transmit the processed signal to a controlled device that is configured to receive the processed signal, and a patient training apparatus configured to receive a patient training signal that causes the patient training apparatus to controllably move, the patient training apparatus being not in contact with the patient. The system may be configured to perform an integrated patient training routine to produce the patient training signal, to store a set of multicellular signal data detected during a movement of the one or more joints, and to correlate the set of multicellular signal data to a second set of data related to the movement of the patient training apparatus.

In another exemplary aspect, a biological interface system may comprise a sensor comprising a plurality of electrodes for detecting multicellular signals emanating from one or more living cells of a patient, a processing unit configured to receive the multicellular signals from the sensor and process the multicellular signals to produce a processed signal, the processing unit being configured to transmit the processed signal to a controlled device, a first controlled device configured to receive the processed signal, and a second controlled device configured to receive the processed signal. The first controlled device may provide feedback to the patient to improve control of the second controlled device.

Another exemplary aspect may provide a method of controlling a device with neural signals emanating from a patient. The method may comprise detecting multicellular signals emanating from one or more living cells of a patient, processing the multicellular signals to produce a processed signal, transmitting the processed signal to a first controlled device and a second controlled device, the first and second controlled devices being configured to receive the processed signal, and providing feedback to the patient with the first controlled device to improve control of the second controlled device.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention. In the drawings.

DESCRIPTION OF THE EMBODIMENTS

Figure 1:
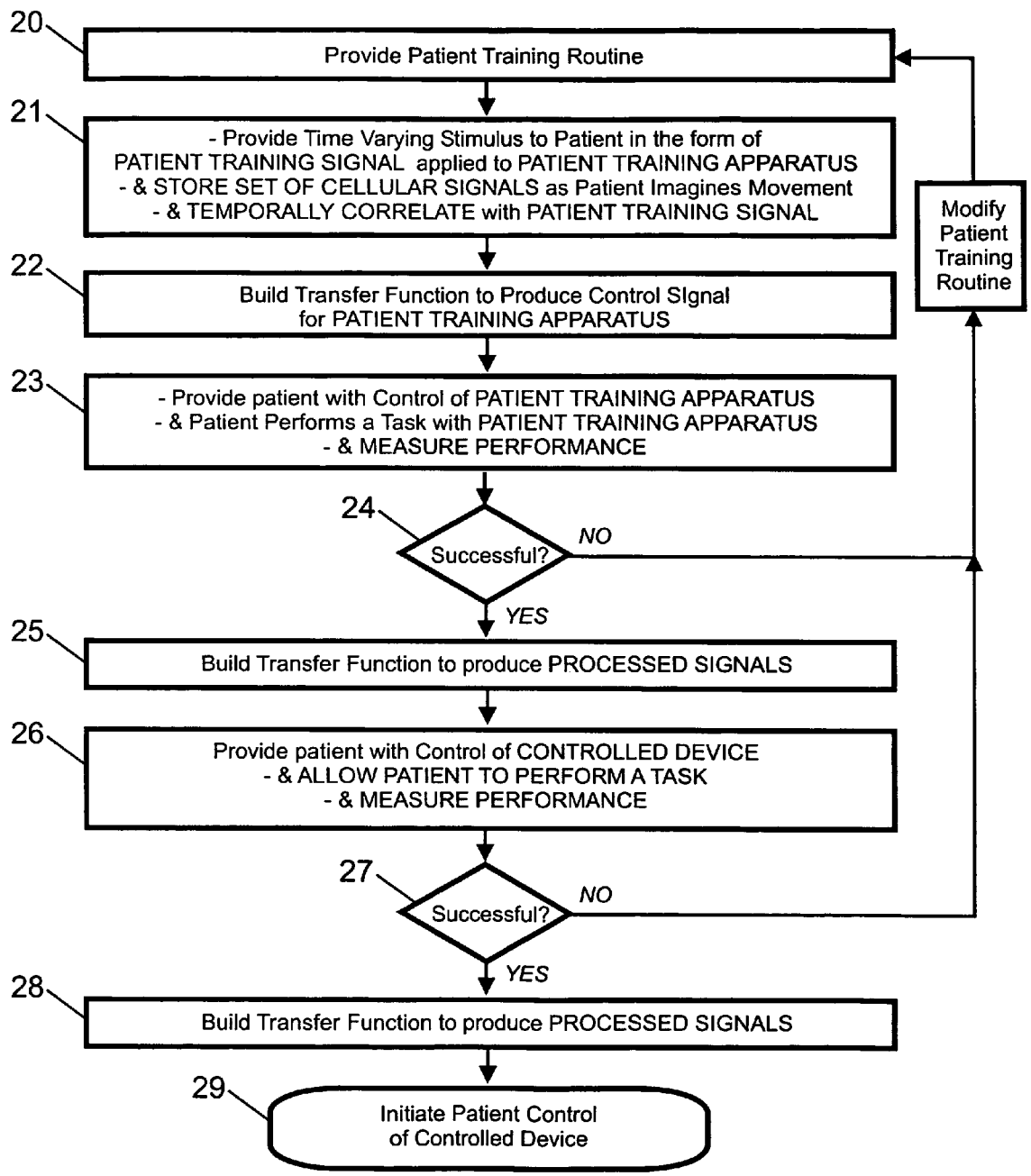
FIG. 1 illustrates a patient training routine flow chart of an exemplary embodiment of a biological interface system consistent with the present invention.

To facilitate an understanding of the invention, a number of terms are defined immediately herebelow.

Definitions

As used herein, the term "biological interface system" refers to a neural interface system or any system that interfaces with living cells that produce electrical activity or cells that produce other types of detectable signals.

The term "cellular signals," as used herein, refers to signals or combination of signals that may emanate from any living cell, such as, for example, subcellular signals, intracellular signals, and extracellular signals. For example, "cellular signals" may include, but not be limited to: neural signals (e.g., neuron action potentials or spikes, local field potential (LFP) signals, electroencephalogram (EEG) signals, electrocorticogram signals (ECoG), and signals whose frequency range falls between single neuron spikes and EEG signals); cardiac signals (e.g., cardiac action potentials); electromyogram (EMG) signals; glial cell signals; stomach cell signals; kidney cell signals; liver cell signals; pancreas cell signals; osteocyte cell signals; sensory organ cell signals (e.g., signals emanating from the eye or inner ear); tumor cell signals; and tooth cell signals.

The term "multicellular signals," as used herein, refers to signals emanating from two or more cells, or multiple signals emanating from a single cell. The term "subcellular signals," as used herein, refers to, for example, a signal derived from a part of a cell, a signal derived from one particular physical location along or within a cell, a signal from a cell extension (e.g., dendrite, dendrite branch, dendrite tree, axon, axon tree, axon branch, pseudopod, or growth cone), and signals from organelles (e.g., golgi apparatus or endoplasmic reticulum). The term "intracellular signals," as used herein, refers to a signal that is generated within a cell or by the entire cell that is confined to the inside of the cell up to and including the membrane. The term "extracellular signals," as used herein, refers to signals generated by one or more cells that occur outside of the cell(s).

As used herein, the term "patient" refers to any animal, such as a mammal and preferably a human. Specific examples of a "patient" include, but are not limited to: individuals requiring medical assistance; healthy individuals; individuals with limited function; and individuals with lost motor or other function due to traumatic injury or neurological disease.

As used herein, the term "configuration" refers to any alteration, improvement, repair, calibration, or other system modifying event whether manual in nature or partially or fully automated. The term "configuration parameter," as used herein, refers to a variable, or a value of the variable, of a component, device, apparatus, and/or system. A configuration parameter has a value that can be: set or modified; used to perform a function; used in a mathematical or other algorithm; used as a threshold value to perform a comparison; and any combinations thereof. A configuration parameter's value determines the characteristics or behavior of something. System configuration parameters are variables of the system of the present invention, such as those used to by the processing unit to produce processed signals.

Other, numerous subsets of configuration parameters are applicable, these subsets including but not limited to: calibration parameters such as a calibration frequency parameter; controlled device parameters such as a time constant parameter; processing unit parameters such as a cell selection criteria parameter; patient parameters such as a patient physiologic parameter such as heart rate; multicellular signal sensor parameters; other sensor parameters; system environment parameters; mathematical algorithm parameters; a safety parameter; and other parameters. Certain parameters may be controlled by the patient's clinician, such as a password-controlled parameter securely controlled by an integral permission routine of the system. Certain parameters may represent a "threshold" such as a success threshold used in a comparison to determine if the outcome of an event was successful. In numerous steps of a system configuration or other function, a minimum performance or other measure may be maintained by comparing a detected signal, or the output of an analysis of one or more signals, to a success threshold.

As used herein, the term "discrete component" refers to a component of a system such as those defined by a housing or other enclosed or partially enclosed structure, or those defined as being detached or detachable from another discrete component. Each discrete component can transmit information to a separate component through the use of a physical cable, including one or more of electrically conductive wires or optical fibers, or transmission of information can be accomplished wirelessly. Wireless communication can be accomplished with a transceiver that may transmit and receive data such as through the use of "Bluetooth" technology or according to any other type of wireless communication means, method, protocol or standard, including, for example, code division multiple access (CDMA), wireless application protocol (WAP), Infrared or other optical telemetry, radio frequency or other electromagnetic telemetry, ultrasonic telemetry or other telemetric technologies.

As used herein, the term "routine" refers to an established function, operation, or procedure of a system, such as an embedded software module that is performed or is available to be performed by the system. Routines may be activated manually such as by an operator of a system, or occur automatically such as a routine whose initiation is triggered by another function, an elapsed time or time of day, or other trigger.

The devices, apparatus, systems and methods of the present invention may include or otherwise have integrated into one or their components, numerous types and forms of routines. An "adaptive processing routine" is activated to determine and/or cause a routine or other function to be modified or otherwise adapt to maintain or improve performance. A competitive routine is activated to provide a competitive function for the patient of the present invention to compete with, such as a function which allows an operator of the system to compete with the patient in a patient training task; or an automated system function which controls a visual object which competes with a patient controlled object. A "configuration routine" is activated to configure one or more system configuration parameters of the system, such as a parameter that needs an initial value assigned or a parameter that needs an existing parameter modified.

A system "diagnostic routine" is activated, automatically or with operator intervention, to check one or more functions of the system to insure proper performance and indicate acceptable system status to one or more components of the system or an operator of the system. A "language selection routine" is activated to change a language displayed in text form on a display and/or in audible form from a speaker. A "patient training routine" is activated to train the patient in the use of the system and/or train the system in the specifics of the patient, such as the specifics of the patient's multicellular signals that can be generated by the patient and detected by the sensor. A "permission routine" is activated when a system configuration or other parameter is to be initially set or modified in a secured manner. The permission routine may use one or more of: a password; a restricted user logon function; a user ID; an electronic key; a electromechanical key; a mechanical key; a specific Internet IP address; and other means of confirming the identify of one or more operators prior to allowing a secure operation to occur. A "remote technician routine" is activated to allow an operator to access the system of the present invention, or an associated device, from a location remote from the patient, or a system component to be modified. A "system configuration routine" is activated to configure the system, or one or more components or associated devices of the system. In a system configuration routine, one or more system configuration parameters may be modified or initially set to a value. A "system reset routine" is activated to reset the entire system or a system function. Resetting the system is sometimes required with computers and computer based devices such as during a power failure or a system malfunction.

General Description of the Embodiments

Systems, methods and devices consistent with the invention detect cellular signals generated within a patient's body and implement various signal processing techniques to generate processed signals for transmission to one or more devices to be controlled. The system includes a sensor, consisting of a plurality of electrodes that detect multicellular signals from one or more living cells, such as from the central or peripheral nervous system of a patient. The system further includes a processing unit that receives and processes the multicellular signals and transmits processed signals to a controlled device. The processing unit utilizes various electronic, mathematics neural net and other signal processing techniques in producing the processed signals.

An integrated patient training routine is embedded in one or more components of the system. The patient training routine may be a requirement of the system prior to allowing full control of the controlled device to the patient. The patient training routine can be utilized to develop a transfer function to apply to the multicellular signals to produce the processed signals. The patient training routine produces a patient training signal that is transmitted to a patient training apparatus. The patient training signal is applied to controllably move the patient training apparatus, providing a time varying stimulus for the patient to imagine one or more movements.

While the patient training apparatus provides the time varying stimulus and the patient imagines the one or more movements, multicellular data received by the processing unit from the sensor is stored in memory. Simultaneously, a second set of data, such as the patient training signal, a derivative of the patient training signal, and/or other sets of data is stored and correlated with the multicellular data. The patient training apparatus may move one or more joints of the patient, or may have no contact with the patient.

In another embodiment of this application, systems, methods and devices consistent with the invention detect cellular signals generated within a patient's body and implement various signal processing techniques to generate processed signals for transmission to two devices to be controlled. The system includes a sensor, consisting of a plurality of electrodes that detect multicellular signals from one or more living cells, such as from the central or peripheral nervous system of a patient. The system further includes a processing unit that receives and processes the multicellular signals and transmits processed signals to both of the controlled devices. The processing unit utilizes various electronic, mathematic, neural net and other signal processing techniques in producing the processed signals. The first controlled device provides feedback to the patient that improves control of the second controlled device.

Detailed Description of the Embodiments

Reference will now be made in detail to the present embodiments of the invention, examples of which are illustrated in the accompanying drawings. Wherever possible, the same reference numbers will be used throughout the drawings to refer to the same or like parts.

Referring now to FIG. 1, a flow chart of the patient training routine of the present invention is illustrated consisting of multiple steps and conditional statements that determine the patient training routine progression from step to step. The patient training routine is preferably a software program, embedded in one or more components of the system such as the processing unit. Alternatively, an additional component is included in the system, such as a computer to configure the system, described in detail in reference to FIG. 5 herebelow, and the patient training routine is embedded in whole or in part in the additional component. The patient training routine may be activated automatically by the system, or an operator of the system, such as the patient's clinician or the patient themselves, may initiate and/or conduct the patient training routine. The patient training routine is preferably used to generate one or more system configuration parameters, such as a configuration parameter used by the processing unit to create a transfer function for producing the processed signals.

Referring back to FIG. 1, Step 20 includes the system providing a patient training routine, consisting of a predetermined, but alterable configuration. The next sequential step 21 includes the providing of a time varying stimulus for the patient to imagine one or more movements. The time varying stimulus is provided in the form of the patient training apparatus with the patient training signal applied. The time varying stimulus can be a prerecorded or other predetermined event, and it be initiated automatically, or by an operator of the system such as a patient utilizing one or more input devices selected from the group consisting of: chin joystick; eyebrow EMG switch; EEG activated switch such as the switched manufactured by BrainFingers of Yellow Springs, Ohio, USA; eye tracker such as the device manufactured by LC Technologies of Fairfax, Va., USA; a head tracker such as the device manufactured Synapse Adaptive of San Rafael, Calif., USA; neck movement switch; shoulder movement switch; Sip n' Puff joystick controller such as the controller manufactured by QuadJoy of Sheboygan, Wis., USA; speech recognition switch; tongue switch such as a tongue palate switch; and any combination thereof. While receiving the time varying stimulus, the patient imagines associated movements or other imagined events associated with the time varying stimulus. Simultaneously, the multicellular signals are stored in one or more components of the system, and temporally correlated with the patient training signal. The time varying stimulus can alternatively be provided real time by an operator of the system.

The patient training apparatus of the present invention may provide the time varying stimulus by moving one or more joints of the patient, such as the patient training apparatus including an exoskeleton device or an FES device implanted in the patient. In these embodiments, the sensor of the present invention is preferably placed in the part of the patient's motor cortex associated with a controlled limb or an amputated limb to be replaced by a prosthetic limb or partial limb. In another preferred embodiment, the patient training apparatus does not contact the patient, such as a prosthetic limb not attached to the patient or a robotic arm. The patient training apparatus preferably provides a time varying visual stimulus, such as being a computer with moving objects, or the moving mechanical devices or moving patient limbs described immediately hereabove. Other forms of time varying stimulus include audible, tactile, olfactory and gustatory stimulus, provided in combination or individually, via one or more patient training apparatus of the present invention.

The patient training apparatus may also be the controlled device, or a separate controlled device may be used after the patient training routine has been successfully completed. An exoskeleton may be used to control a mannequin or other suitable structure, or even a human or other mammal that is not the patient, while the patient training routine is performed, after which it is attached to the patient to be the controlled device controlled by the processed signals. An FES series of implants can be used as the patient training apparatus and the controlled device, and/or the an alternative controlled device can be used such as a controlled computer cursor, mouse, joystick or keypad, wherein the FES control is preferred during the patient training event. A robotic arm can be used as the patient training apparatus, wherein it may be attached to a patient limb or digit, or be separated in distance from the patient. A robotic device can be attached to the patient's hand or other moveable body part, such as is described in detail in reference to FIG. 2 and FIG. 3 herebelow, the robotic device controllably moving the patient's hand in two or three dimensions. In another preferred embodiment, a second patient training apparatus is included, used simultaneously with the first patient training apparatus or in serial fashion. The second patient training apparatus may receive the same patient training signal as the first or a different patient training signal. Numerous forms of patient training apparatus can be utilized in the performance of the patient training routine of the present invention, such as one or more vehicles selected from the group consisting of: aircraft, helicopter; car; tank; wheelchair; and any combination thereof.

The correlation between the multicellular signals and the patient training signal is preferably a temporal correlation. An alternative of the patient training signal used in the correlation is a mathematically processed version, a derivative version, of the patient training signal. Other alternatives include derivative of one or motions of the patient training apparatus, such as from a sensor, visual recording device, image processed visual recording, or other source. Other alternatives or additions for correlation include but are not limited to: a patient physiologic parameter such as heart rate; a controlled device parameter; a system environment parameter; a password controlled parameter; a clinician controlled parameter; a patient training routine parameter; and combinations of the preceding. The basis of the correlation may include the matching of one or more periodicities of the set of multicellular signals and the second set of data. A periodicity of motion or other parameter of the time varying stimulus or the patient may be matched to a similar periodicity in the set of the multicellular signals.

Referring back to FIG. 1, the next sequential step 22 includes the building of a transfer function that is utilized by the processing unit to produce the processed signals for a device to be controlled. The transfer function is a mathematical equation that is applied to the multicellular signals received from the sensor of the present invention by the processing unit. In addition to the multicellular signals, the transfer function is generated using the second set of data that has been correlated to the multicellular signals. In the next sequential step 23, the patient is provided control of the patient training apparatus via the processed signals created by applying the above transfer function to the multicellular signals received by the processing unit. The patient performs one or more tasks with the patient training apparatus, as defined by the patient training routine, and a performance measurement is made. In comparative step 24, the performance measurement is compared to a threshold value, such as a threshold value that can be set or modified by an operator, such as by a clinician, such as by the use of a permission routine of the system. If the performance measurement is below the threshold, the next sequential step is a repeat of step 20, wherein the patient training routine is provided, and the above sequence repeated until an adequate performance is achieved. Prior to providing the patient training routine, the patient training routine may be modified, such as an automatic modification made by the system based on one or more results of steps 21 through 24, or the patient training routine may be left unchanged and simply repeated. An operator may modify the patient training routine, such as an operator at a remote location in communication with the system via the Internet.

If the performance measurement of step 23 is at or above the threshold, the next sequential step 25 is performed. Another transfer function is generated, such as the same transfer function when the patient training apparatus is the controlled device, or a different transfer function when the patient training apparatus and the controlled device are different. In the next sequential step 26, the patient is provided control of the controlled device via the processed signals created by applying the transfer function of step 25 to the multicellular signals received by the processing unit. The patient performs one or more tasks with the controlled device, as defined by the patient training routine, and a second performance measurement is made. In comparative step 27, the performance measurement is compared to a threshold value, such as a threshold value that can be set or modified by an operator, such as by a clinician, such as by the use of a permission routine of the system. If the performance measurement is below the threshold, the next sequential step is a repeat of step 20, wherein the patient training routine is provided, and the above sequence repeated until an adequate performance is achieved. Prior to providing the patient training routine, the patient training routine may be modified, such as an automatic modification made by the system based on one or more results of steps 21 through 27, or the patient training routine may be left unchanged and simply repeated.

If the performance measurement of step 27 is at or above the controlled device threshold, the next sequential step 28 is performed. Another transfer function is generated, such as the same transfer function of step 25 or a new transfer function. In the next sequential step 29, the patient is provided control of the controlled device via the processed signals created by applying the transfer function of step 28 to the multicellular signals received by the processing unit. The patient is preferably provided unlimited, or full control of the control device. In an alternative embodiment, the patient is given limited control of the controlled device, and a subsequent patient training routine must be successfully performed for the patient to achieve full control of the controlled device.

The patient training routine of the present invention may include one or more forms of feedback to the patient in addition to the time varying stimulus, or as an additional time varying stimulus. The feedback may be a derivative of the multicellular signals such as neural spike modulation rates. The feedback may be of the form selected from the group consisting of: auditory; olfactory; taste; visual; electrical stimulation; and any combination thereof. The feedback may be a representation of the processed signal, such feedback selected from the group consisting of: moving object on screen; moving mechanical device such as a mechanical limb or wheelchair; moving part of patient's body such as via an exoskeleton device or FES device; changing audible signal such as a multi-frequency signal; and any combination thereof. The feedback may include an indication of the difference between a desired level of control and an actual level of control, such as when the patient is attempting to track a motion or a predictory path of motion. In a preferred embodiment, the patient controlled feedback may be artificially improved, such as to improve the training procedure, wherein the artificial improvement factor may decrease as the actual control increases.

Figure 2:
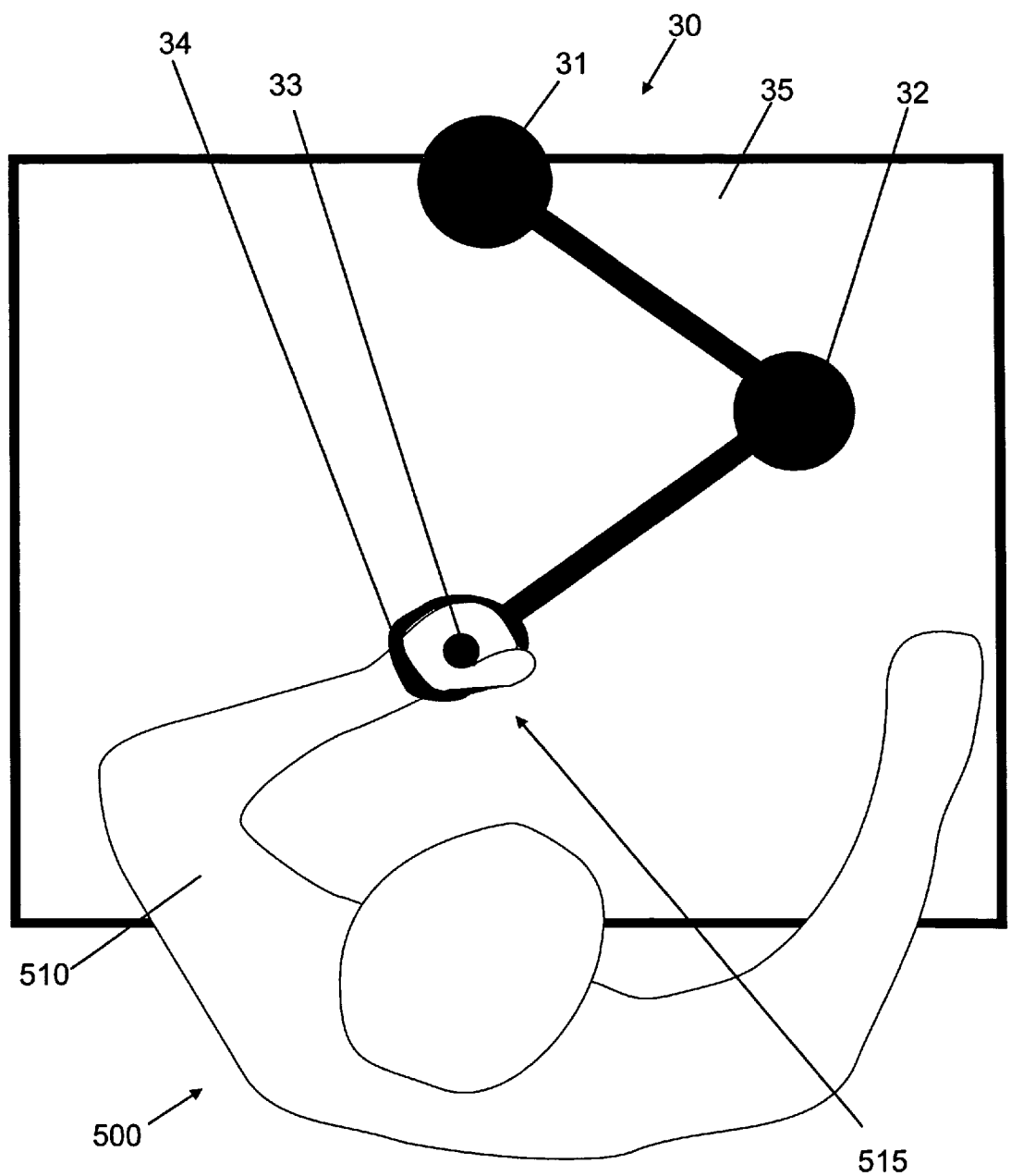
FIG. 2 illustrated a patient training apparatus of an exemplary embodiment of a biological interface system consistent with the present invention.

Referring now to FIG. 2, a patient training apparatus of the present invention is illustrated wherein a controllable robotic arm causes the hand of the patient to move in a range of values within a two-dimensional space. In an alternative embodiment, the patient's hand is moved in a three dimensional space. Patient 500 is illustrated sitting, such as in a wheelchair, in front of hand position controller 30, a preferred embodiment of a patient training apparatus of the present invention. Hand position controller includes two servos, first servo 31 and second servo 32 which are controlled by a patient training signal of the present invention two move spindle 33 within a pre-defined area of desk 35. Patient 500 is a patient with impaired motor function of at least left arm 510, such as a quadriplegic patient. Hand 515 is attached to spindle 33 with removable band 34 such that controlled positioning of spindle 33 by the controlled rotation and positioning of servo 31 and servo 32 causes patient 500's hand 515 to also move in the same pattern.

In the patient training event of the present invention, the time varying stimulus is the movement of the patient's hand as determined by the patient training signal and hand position controller 30. In a preferred embodiment, the sensor of the present invention is placed in or near one or more nerve cells associated with movement of the part of the patient's body being moved, such as the left hand of patient 500 of FIG. 2, such nerve cells including but not limited to: cells of the motor cortex and cells of the spinal cord. Alternative embodiments of hand position controller 30 can be utilized without departing from the spirit and scope of this application such as other robotic or controlled mechanisms that move one or more parts of the patient's body to provide a time varying stimulus for an imagined movement.

Figure 3:
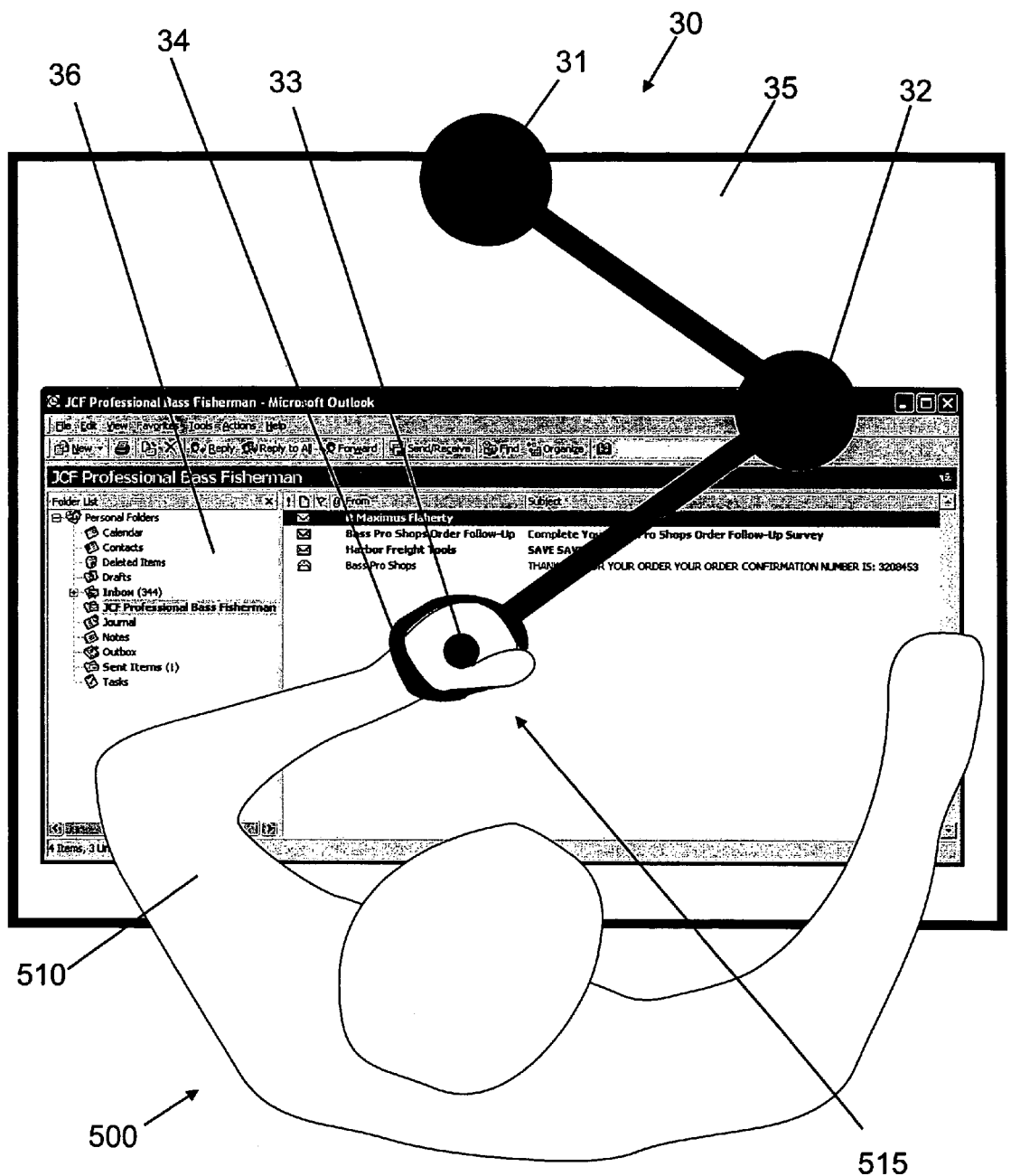
FIG. 3 illustrates a surrogate controlled device of an exemplary embodiment of a biological interface system consistent with the present invention.

Referring now to FIG. 3, an alternative embodiment of the biological interface system is disclosed. The biological interface system collects multicellular signals emanating from one or more living cells of a patient and for transmitting processed signals to two controlled devices. The system includes a sensor for detecting the multicellular signals, the sensor consisting of a plurality of electrodes to allow for detection of the multicellular signals. A processing unit receives the multicellular signals from the sensor, processes the multicellular signals to produce processed signals, and transmits the processed signals to both controlled devices. Both the first controlled device and the second controlled device receive the processed signals, such as identical or different processed signals. The difference in the processed signals may be based solely on the differences between the two controlled devices. The first controlled device provides feedback to the patient that results in improved control of the second controlled device.

Hand position controller 30 is of similar configuration and construction to hand position controller 30 of FIG. 2, with all the similar components defined with the same reference numbers. Hand position controller 30, alternatively or additionally, is used in the embodiment depicted in FIG. 3 as a controlled device of the biological interface system of the present invention. A second controlled device, such as a computer mouse and/or cursor, not shown, also receives processed signals from the processing unit, not shown. Used as a controlled device, a projected image, such as an image shown from below wherein desk 35 includes a horizontal monitor, or from above wherein a projector, not shown, projects the image onto desk 35. Patient 500 visualizes a computer screen that matches the second controlled device computer screen. By controlling hand position controller 30 with the processed signals, and receiving the feedback provided by projection 36, patient 500 receives feedback similar to a non-motor impaired person controlling a computer with a mouse. The feedback is also appropriate because the sensor of patient 500 is preferably placed in the part of the motor cortex associated with the left arm and hand.

Other forms of feedback can be included with the biological interface apparatus of FIG. 3 including: visual; auditory; olfactory; gustatory; tactile; and any combination thereof. Numerous configurations of the first and second controlled devices can be used, such as configuration in which the first controlled device performs a surrogate function that provides feedback or other advantages that result in improved control of the second controlled device. The first controlled device may be a smaller version of the second controlled device, such as a scaled model of the second controlled device. The first controlled device may be a computer, while the second device is not a computer. In this configuration, the computer may provide a controlled animation of the second controlled device. In alternative embodiments, the second controlled device may be at a location remote from the patient. The first controlled device may have very different feedback or other controllable features such as the first device being an audible transducer and the second controlled device is a computer, robotic arm, FES device and/or exoskeleton device. In this configuration, the first controlled device may assume a hearing aid configuration, fitted to the patient's ear to provide the audio feedback.

Figure 4:
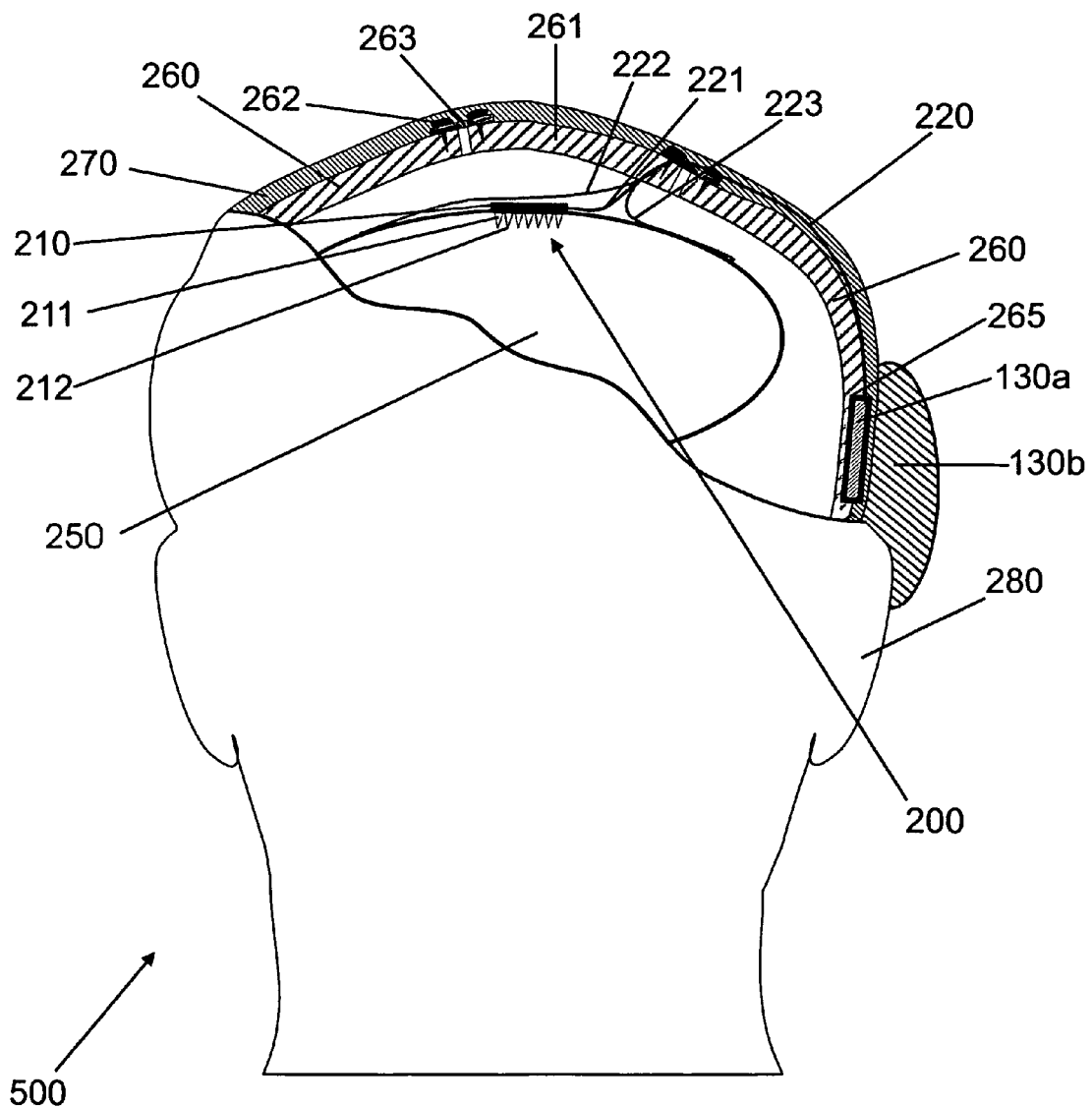
FIG. 4 illustrates an exemplary embodiment of a portion of the biological interface system consistent with the present invention wherein sensor electrodes are implanted in the brain of a patient and a portion of a processing unit is implanted on the skull of the patient.

Referring now to FIG. 4, a brain implant apparatus consistent with an embodiment of the present invention is illustrated. As shown in FIG. 4, the system includes an array of electrodes assembly, sensor 200, which has been inserted into a brain 250 of patient 500, through a previously created opening in scalp 270 and skull 260 in a surgical procedure known as a craniotomy. Sensor 200 includes a plurality of longitudinal projections 211 extending from a base, array substrate 210. Projections 211 may be rigid, semi-flexible or flexible, the flexibility such that each projection 211 can still penetrate into neural tissue, potentially with an assisting device or with projections that only temporarily exist in a rigid condition. Sensor 200 has been inserted into brain 250, preferably using a rapid insertion tool, such that the projections 211 pierce into brain 250 and sensor substrate 210 remains in close proximity to or in light contact with the surface of brain 250. At the end of each projection 211 is an electrode, electrode 212. In alternative embodiments, electrodes can be located at a location other than the tip of projections 211 or multiple electrodes may be included along the length of one or more of the projections 211. One or more projections 211 may be void of any electrode, such projections potentially including anchoring means such as bulbous tips or barbs, not shown.

Electrodes 212 are configured to detect electrical brain signals or impulses, such as individual neuron spikes or signals that represent clusters of neurons such as local field potential (LFP) and electroencephalogram (EEG) signals. Each electrode 212 may be used to individually detect the firing of multiple neurons, separated by neuron spike discrimination techniques. Other applicable signals include electrocorticogram (ECoG) signals and other signals, such as signals between single neuron spikes and EEG signals. Sensor 200 may be placed in any location of a patient's brain allowing for electrodes 212 to detect these brain signals or impulses. In a preferred embodiment, electrodes 212 can be inserted into a part of brain 250 such as the cerebral cortex. Alternative forms of penetrating electrodes, such as wire or wire bundle electrodes, can make up or be a component of the sensor of the present invention. In addition to or alternative from neural signals, the system of the present invention may utilize other types of cellular signals to produce processed signals to control a device. The various forms of penetrating electrodes described above can be placed into tissue within or outside of the patient's cranium, such tissue including but not limited to: nerve tissue such as peripheral nerve tissue or nerves of the spine; organ tissue such as heart, pancreas, liver or kidney tissue; tumor tissue such as brain tumor or breast tumor tissue; other tissue and combinations of the preceding.

Alternatively or additionally, the sensor of the present invention may employ non-penetrating electrode configurations, not shown, such as subdural grids placed inside the cranium such as to record LFP signals. In addition to subdural grids, the sensor may consist of or otherwise include other forms of non-penetrating electrodes such as flat electrodes, coil electrodes, cuff electrodes and skin electrodes such as scalp electrodes. These non-penetrating electrode configurations are placed in, on, near or otherwise in proximity to the cells whose signals are to be detected, such as neural or other cellular signals. In another alternative embodiment, the sensor of the present invention includes detectors other than electrodes, such as photodetectors that detect cellular signals represented by a light emission. The light emission can be caused by a photodiode, integrated into the sensor or other implanted or non-implanted system component, shining one or more wavelengths of light on the appropriate cells. In addition to the numerous types of cells described above, one or more of the various configurations of the sensor of the present invention may utilize any living cell of the body that emanates cellular signals. In a preferred embodiment, the cellular signals are under voluntary control of the patient.

Although FIG. 4 depicts sensor 200 as a single discrete component, in alternative embodiments the sensor consists of multiple discrete components, including one or more types of electrodes or other cellular signal detecting elements, each configured and placed to detect similar or dissimilar types of cellular signals. Multiple sensor discrete components can be implanted entirely within: the skull, an extracranial location such as a peripheral nerve, or external to the body; or the components can be placed in any combination of these locations.

Sensor 200 serves as the multicellular signal sensor of the biological interface system of the present invention. While FIG. 4 shows sensor 200 as eight projections 211 with eight electrodes 212, sensor 200 may include one or more projections with and without electrodes, both the projections and electrodes having a variety of sizes, lengths, shapes, surface areas, forms, and arrangements. Moreover, sensor 200 may be a linear array (e.g., a row of electrodes) or a two-dimensional array (e.g., a matrix of rows and columns of electrodes such as a ten by ten array), or wire or wire bundle electrodes, all well known to those of skill in the art. An individual wire lead may include a plurality of electrodes along its length. Projections and electrodes may have the same materials of construction and geometry, or there may be varied materials and/or geometries used in one or more electrodes. Each projection 211 and electrode 212 of FIG. 4 extends into brain 250 to detect one or more cellular signals such as those generated form the neurons located in proximity to each electrode 212's placement within the brain. Neurons may generate such signals when, for example, the brain instructs a particular limb to move in a particular way and/or the brain is planning that movement. In a preferred embodiment, the electrodes reside within the arm, hand, leg or foot portion of the motor cortex of the brain. The processing unit of the present invention may assign one or more specific cellular signals to a specific use, such as a specific use correlated to a patient imagined event. In a preferred embodiment, the one or more cellular signals assigned to a specific use are under voluntary control of the patient.

Referring back to FIG. 4, the processing unit of the present invention includes processing unit first portion 130a, placed under the scalp at a location near patient 500's ear 280. Processing unit first portion 130a receives cellular signals from sensor 200 via wire bundle 220, a multi-conductor cable. In a preferred embodiment, wire bundle 220 includes a conductor for each electrode 212. Processed signals are produced by processing unit first portion 130a and other processing unit discrete components, such as processing unit second portion 130b removably placed on the external skin surface of patient 500 near ear 280. Processing unit second portion 130b remains in relative close proximity to implanted component processing unit first portion 130a through one or more fixation means such as cooperative magnetic means in both components, or body attachment means such as where the processing unit second portion 130b is attached to eye glasses, an ear wrapping arm, a hat, mechanical straps or an adhesive pad. Processing unit first portion 130a and processing unit second portion 130b work in combination to receive multicellular signal data and create a time code of brain activity.

In the preferred embodiment depicted in FIG. 4, bone flap 261, the original bone portion removed in the craniotomy, has been used to close the hole made in the skull 260 during the craniotomy, obviating the need for a prosthetic closure implant. Bone flap 261 is attached to skull 260 with one or more straps, bands 263, which are preferably titanium or stainless steel. Band 263 is secured to bone flap 261 and skull 260 with bone screws 262. Wire bundle 220 passes between bone flap 261 and the hole cut into skull 260. During the surgical procedure, bone recess 265 was made in skull 260 such that processing unit first portion 130a could be placed in the indentation, allowing scalp 270 to lie relatively flat and free of tension in the area proximal to processing unit first portion 130a. A long incision in scalp 270 between the craniotomy site and the recess 265 can be made to place processing unit first portion 130a in recess 265. Alternatively, an incision can be made to perform the craniotomy, and a separate incision made to form recess 265, after which the processing unit first portion 130a and wire bundle 220 can be tunneled under scalp 270 to the desired location. Processing unit first portion 130a is attached to skull 260 with one or more bone screws or a biocompatible adhesive, not shown.

In an alternative embodiment, processing unit first portion 130a may be placed entirely within skull 260 or be geometrically configured and surgically placed to fill the craniotomy hole instead of bone flap 261. Processing unit first portion 130a can be placed in close proximity to sensor 200, or a distance of 5-20 cm can separate the two components. Processing unit first portion 130a includes a biocompatible housing which creates a fluid seal around wire bundle 220 and numerous internal components of processing unit first portion 130a, internal components not shown. Processing unit first portion 130a internal components provide the following functions: signal processing of the cellular signals received from sensor 200 such as buffering, amplification, digital conversion and multiplexing, wireless transmission of cellular signals, a partially processed, or derivative form of the cellular signals, or other data; inductive power receiving and conversion; and other functions well known to implanted electronic assemblies such as implanted pacemakers, defibrillators and pumps.

Processing unit second portion 130b, removably placed at a location proximate to implanted processing unit first portion 130a but external to patient 500, receives data from processing unit first portion 130a via wireless communication through the skin, such as infrared or radiofrequency wireless data transfer means. Processing unit second portion 130b, includes, in addition to wireless data receiving means, wireless power transfer means such as an RF coil which inductively couples to an implanted coil, signal processing circuitry, an embedded power supply such as a battery, and data transfer means. The data transfer means of processing unit second portion 130b may be wired or wireless, and transfer data to one or more of: implanted processing unit first portion 130a; a different implanted device; and an external device such as an additional component of the processing unit of the present invention, a controlled device of the present invention or a computer device such as a configuration computer with Internet access, all not shown.

Referring back to FIG. 4, electrodes 212 transfer the detected cellular signals to processing unit first portion 130a via array wires 221 and wire bundle 220. Wire bundle 220 includes multiple conductive elements, and array wires 221, which preferably include a conductor for each electrode of sensor 200. Also included in wire bundle 220 are two conductors, first reference wire 222 and second reference wire 223 each of which is placed in an area in relative proximity to sensor 200 such as on the surface of brain 250 near the insertion location. First reference wire 222 and second reference wire 223 may be redundant, and provide reference signals used by one or more signal processing elements of the processing unit of the present invention to process the cellular signal data detected by one or more electrodes. In an alternative embodiment, not shown, sensor 200 consists of multiple discrete components and multiple bundles of wires connect to one or more discrete components of the processing unit, such as processing unit first portion 130a. In another alternative embodiment, not shown, cellular signals detected by sensor 200 are transmitted to processing unit 130a via wireless technologies, such as infrared communication incorporated into an electronic module of sensor 200, such transmissions penetrating the skull of the patient, and obviating the need for wire bundle 220, array wires 221 and any physical conduit passing through skull 260 after the surgical implantation procedure is completed.

Processing unit first portion 130a and processing unit second portion 130b independently or in combination preprocess the received cellular signals (e.g., impedance matching, noise filtering, or amplifying), digitize them, and further process the cellular signals to extract neural data that processing unit second portion 130b may then transmit to an external device (not shown), such as an additional processing unit component and/or any device to be controlled by the processed multicellular signals. For example, the external device may decode the received neural data into control signals for controlling a prosthetic limb or limb assist device or for controlling a computer cursor. In an alternative embodiment, the external device may analyze the neural data for a variety of other purposes. In another alternative embodiment, the device receiving transmissions from processing unit second portion 130b is an implanted device. Processing unit first portion 130a and processing unit second portion 130b independently or in combination include signal processing circuitry to perform multiple signal processing functions including but not limited to: amplification, filtering, sorting, conditioning, translating, interpreting, encoding, decoding, combining, extracting, sampling, multiplexing, analog to digital converting, digital to analog converting, mathematically transforming and/or otherwise processing cellular signals to generate a control signal for transmission to a controlled device. Processing unit first portion 130a and processing unit second portion 130b may include one or more components to assist in processing the multicellular signals or to perform additional functions. These components include but are not limited to: a temperature sensor; a pressure sensor; a strain gauge; an accelerometer; a volume sensor; an electrode; an array of electrodes; an audio transducer; a mechanical vibrator; a drug delivery device; a magnetic field generator; a photo detector element; a camera or other visualization apparatus; a wireless communication element; a light producing element; an electrical stimulator; a physiologic sensor; a heating element and a cooling element.

Processing unit first portion 130a transmits raw or processed cellular signal data to processing unit second portion 130b through integrated wireless communication means, such as the infrared communication means of FIG. 4, or alternative means including but not limited to radiofrequency communications, other optical communications, inductive communications, ultrasound communications and microwave communications. In a preferred, alternate embodiment, processing unit first portion 130a includes both infrared communication means for short-range high baud rate communication, and radiofrequency communication means for longer range, lower baud rate communication. This wireless transfer allows sensor 200 and processing unit first portion 130a to be completely implanted under the skin of the patient, avoiding the need for implanted devices that require protrusion of a portion of the device or wired connections through the skin surface. In an alternative embodiment, a through the skin pedestal connector is utilized between either the implanted sensor 200 or processing unit first portion 130a and an external component. Processing unit first portion 130a includes a coil, not shown, which receives power through inductive coupling, on a continual or intermittent basis from an external power transmitting device such as processing unit second portion 130b. The inductive coupling power transfer configuration obviates the need for any permanent power supply, such as a battery, integral to processing unit first portion 130a.

In addition to or in place of power transmission, the integrated coil of processing unit first portion 130a and its associated circuitry may receive data from an external coil whose signal is modulated in correlation to a specific data signal. The power and data can be delivered to processing unit first portion 130a simultaneously such as through simple modulation schemes in the power transfer that are decoded into data for processing unit first portion 130a to use, store or facilitate another function. A second data transfer means, in addition to a wireless means such as an infrared LED, can be accomplished by modulating a signal in the coil of processing unit first portion 130a that data is transmitted from the implant to an external device including a coil and decoding elements. In a preferred embodiment, the processing unit first portion 130a included an embedded ID, which can be wirelessly transmitted to the processing unit second portion 130b or a separate discrete component via the various wireless transmission means described above. In another preferred embodiment, processing unit second portion 130b includes means of confirming proper ID from processing unit first portion 130a and processing unit second portion 130b also included an embedded ID.

Processing unit first portion 130a and processing unit second portion 130b may independently or in combination also conduct adaptive processing of the received cellular signals by changing one or more parameters of the system to achieve acceptable or improved performance. Examples of adaptive processing include, but are not limited to, changing a system configuration parameter during a system configuration, changing a method of encoding neural or other cellular signal data, changing the type, subset, or amount of cellular signal data that is processed, or changing a method of decoding neural or other cellular signal data. Changing an encoding method may include changing neuron spike sorting methodology, calculations, thresholds, or pattern recognition methodologies. Changing a decoding methodology may include changing variables, coefficients, algorithms, and/or filter selections. Other examples of adaptive processing may include changing over time the type or combination of types of signals processed, such as EEG, ECoG, LFP, neural spikes, or other cellular signal types.

Processing unit first portion 130a and processing unit second portion 130b may independently or in combination also transmit electrical signals to one or more electrodes 212 such as to stimulate, polarize, hyperpolarize or otherwise cause an effect on one or more cells of neighboring tissue. Specific electrodes may record cellular signals only, or deliver energy only, and specific electrodes may provide both functions. In an alternative embodiment, a separate device, not shown but preferably an implanted device with the ability to independently or in combination provide an electrical signal to multiple electrodes, delivers stimulating energy to one or more electrodes 212 or different electrodes, also not shown. Stimulating electrodes in various locations can transmit signals to the central nervous system, peripheral nervous system, other body systems, body organs, muscles and other tissue or cells. The transmission of these signals is used to perform one or more functions including but not limited to: pain therapy; muscle stimulation; seizure disruption; stroke rehabilitation; coma recovery; and patient feedback.

In an alternative embodiment, not shown, processing unit first portion 130a, and potentially additional signal processing functions are integrated into sensor 200, such as through the use of a bonded electronic microchip. In another alternative embodiment, processing unit first portion 130a may also receive non-neural cellular signals and/or other biologic signals, such as from an implanted sensor. These signals may be in addition to received neural multicellular signals, and they may include but are not limited to: EKG signals, respiration signals, blood pressure signals, electromyographic activity signals and glucose level signals. Such biological signals may be used to change the state of the biological interface system of the present invention, or one of its discrete components. Such state changes include but are not limited to: turn system or component on or off; to begin a configuration routine; to initiate or conclude a step of a configuration or other routine; and to start or stop another system function. In another alternative embodiment, processing unit first portion 130a and processing unit second portion 130b independently or in combination produce one or more additional processed signals, to additionally control the controlled device of the present invention or to control one or more additional controlled devices.

In an alternative, preferred configuration of implanted components, not shown, a discrete component such as a sensor of the present invention is implanted within the cranium of the patient, such as sensor 200 of FIG. 4, a processing unit or a portion of a processing unit of the present invention is implanted in the torso of the patient, and one or more discrete components are external to the body of the patient. The processing unit may receive multicellular signals from the sensor via wired, including conductive wires and optic fibers, or wireless communication. The sensor 200 preferably includes signal processing means including signal processing up to and including digitizing the multicellular signals. In another alternative embodiment, preferably an acute (less than 24 hours) or sub-chronic (less than 30 days) application, a through the skin, or transcutaneous device is used to transmit or enable the transmission of the multicellular signals, and/or a derivative or pre-processed form of the multicellular signals.

Figure 5:
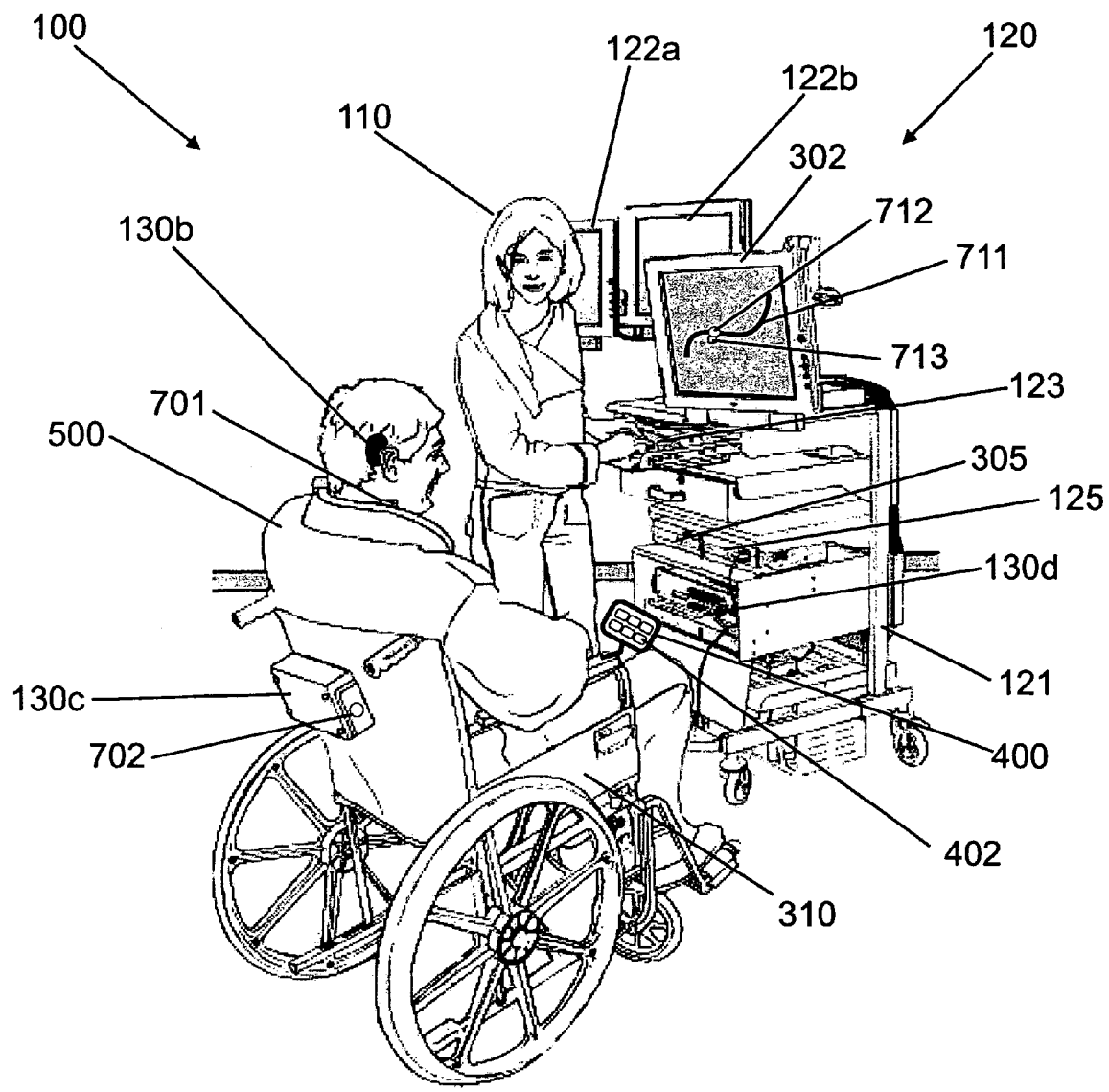
FIG. 5 illustrates another exemplary embodiment of a biological interface system consistent with the present invention wherein an operator configures the system at the patient site.

Referring now to FIG. 5, a biological interface system 100 is shown consisting of implanted components, not shown, and components external to the body of a patient 500. A sensor for detecting multicellular signals, not shown and preferably a two dimensional array of multiple protruding electrodes, has been implanted in the brain of patient 500, in an area such as the motor cortex. In a preferred embodiment, the sensor is placed in an area to record multicellular signals that are under voluntary control of the patient. Alternatively or additionally to the two dimensional array, the sensor may include one or more wires or wire bundles which include a plurality of electrodes. Patient 500 of FIG. 5 is shown as a human being, but other mammals and life forms that produce recordable multicellular signals would also be applicable. Patient 500 may be a patient with a spinal cord injury or afflicted with a neurological disease that has resulted in a loss of voluntary control of various muscles within the patient's body. Alternatively or additionally, patient 500 may have lost a limb, and system 100 will include a prosthetic limb as its controlled device. Numerous types of patients, including healthy individuals, are applicable to the system of the present invention. The patient of the present invention may be a quadriplegic, a paraplegic, an amputee, a spinal cord injury victim or an otherwise physically impaired person. Alternatively or in addition, Patient 500 may have been diagnosed with one or more of: obesity, an eating disorder, a neurological disorder, a psychiatric disorder, a cardiovascular disorder, an endocrine disorder, sexual dysfunction, incontinence, a hearing disorder, a visual disorder, sleeping disorder, a movement disorder, a speech disorder, physical injury, migraine headaches or chronic pain. System 100 can be used to treat one or more medical conditions of patient 500, or to restore, partially restore, replace or partially replace a lost function of patient 500.

Alternatively, system 100 can be utilized by patient 500 to enhance performance, such as if patient 500 did not have a disease or condition from which a therapy or restorative device could provide benefit, but did have an occupation wherein thought control of a device provided an otherwise unachieved advancement in healthcare, crisis management and national defense. Thought control of a device can be advantageous in numerous healthy individuals including but not limited to: a surgeon, such as an individual surgeon using thought control to maneuver three or more robotic arms in a complex laparoscopic procedure or a surgeon controlling various instruments at a location remote from the instruments and the surgical procedure; a crisis control expert, such as a person who in attempting to minimize death and injury uses thought control to communicate different pieces of information and/or control multiple pieces of equipment, such as urban search and rescue equipment, simultaneously during an event such as an earthquake or other disaster, both natural disasters and those caused by man; a member of a bomb squad, such as an expert who uses thoughts to control multiple robots and/or robotic arms to remotely diffuse a bomb; and military personnel who use thought control to communicate with personnel and control multiple pieces of defense equipment, such as artillery, aircraft, watercraft, land vehicles and reconnaissance robots. It should be noted that the above advantages of system 100 to a healthy individual are also advantages achieved in a patient such as a quadriplegic or paraplegic. In other words, a quadriplegic could provide significant benefit to society, such as in controlling multiple bomb diffusing robots, in addition to his or her ambulation and other quality of life devices. Patients undergoing implantation and use of the system 100 of the present invention may provide numerous occupational and other functions not available to individuals that do not have the biological interface system of the present invention.

The sensor electrodes of system 100 can be used to detect various multicellular signals as has been described in detail in reference to FIG. 4 hereabove. The sensor is connected via a multi-conductor cable, not shown but also implanted in patient 500, to an implanted portion of the processing unit which includes some signal processing elements as well as wireless communication means as has been described in detail in reference to FIG. 4. The implanted multi-conductor cable preferably includes a separate conductor for each electrode, as well as additional conductors to serve other purposes, such as providing reference signals and ground. A second portion of the processing unit, processing unit second portion 130*b* receives the wireless communications from the implanted portion. Processing unit second portion 130*b* is removably located just above the ear of patient 500, such as to be aligned with an infrared data transmission element of the implanted device. Multicellular signals or derivatives of the multicellular signals are transmitted from the implanted processing unit component to processing unit second portion 130*b* for further processing. The processing unit components of system 100 perform various signal processing functions as have been described in detail in reference to FIG. 4. The processing unit may process signals that are mathematically combined, such as the combining of neuron spikes that are first separated using spike discrimination methods, these methods known to those of skill in the art. In alternative embodiments, the processing unit may consist of multiple components or a single component; each of the processing unit components can be fully implanted in patient 500, be external to the body, or be implanted with a portion of the component exiting through the skin.

In FIG. 5, a first controlled device is a computer, CPU 305 that is attached to monitor 302 and integrated into configuration cart 121. Through the use of system 100, patient 500 can control one or more computer functions including but not limited to: an on/off function, a reset function, a language function, a modem function, a printer function, an Internet function, a cursor, a keyboard, a joystick, a trackball or other input device. Each function may be controlled individually or in combination. System 100 includes a second controlled device, wheelchair 310. Numerous other controlled devices can be included in the systems of this application, individually or in combination, including but not limited to: a computer; a computer display; a mouse; a cursor; a joystick; a personal data assistant; a robot or robotic component; a computer controlled device; a teleoperated device; a communication device or system; a vehicle such as a wheelchair; an adjustable bed; an adjustable chair; a remote controlled device; a Functional Electrical Stimulator device or system; a muscle stimulator; an exoskeletal robot brace; an artificial or prosthetic limb; a vision enhancing device; a vision restoring device; a hearing enhancing device; a hearing restoring device; a movement assist device; medical therapeutic equipment such as a drug delivery apparatus; medical diagnostic equipment such as epilepsy monitoring apparatus; other medical equipment such as a bladder control device, a bowel control device and a human enhancement device; closed loop medical equipment and other controllable devices applicable to patients with some form of paralysis or diminished function as well as any device that may be utilized under direct brain or thought control in either a healthy or unhealthy patient.

Processing unit second portion 130b includes a unique electronic ID, such as a unique serial number or any alphanumeric or other retrievable, identifiable code associated uniquely with the system 100 of patient 500. The unique electronic identifier may take many different forms in processing unit second portion 130b, such as a piece of electronic data stored in a memory module; a semiconductor element or chip that can be read electronically via serial, parallel or telemetric communication; pins or other conductive parts that can be shorted or otherwise connected to each other or to a controlled impedance, voltage or ground, to create a unique code; pins or other parts that can be masked to create a binary or serial code; combinations of different impedances used to create a serial code that can be read or measured from contacts, features that can be optically scanned and read by patterns and/or colors; mechanical patterns that can be read by mechanical or electrical detection means or by mechanical fit, a radio frequency ID or other frequency spectral codes sensed by radiofrequency or electromagnetic fields, pads and/or other marking features that may be masked to be included or excluded to represent a serial code, or any other digital or analog code that can be retrieved from the discrete component.

Alternatively or in addition to embedding the unique electronic ID in processing unit second portion 130b, the unique electronic ID can be embedded in one or more implanted discrete components. Under certain circumstances, processing unit second portion 130b or another external or implanted component may need to be replaced, temporarily or permanently. Under these circumstances, a system compatibility check between the new component and the remaining system components can be confirmed at the time of the repair or replacement surgery through the use of the embedded unique electronic ID. The unique electronic ID can be embedded in one or more of the discrete components at the time of manufacture, or at a later date such as at the time of any clinical procedure involving the system, such as a surgery to implant the sensor electrodes into the brain of patient 500. Alternatively, the unique electronic ID may be embedded in one or more of the discrete components at an even later date such as during a system configuration routine such as a calibration routine.

Referring again to FIG. 5, processing unit second portion 130b communicates with one or more discrete components of system 100 via wireless communication means. Processing unit second portion 130b communicates with selector module 400, a component utilized to select the specific device or devices to be controlled by the processed signals of system 100. Selector module 400 includes a touch screen set of buttons, input element 402, used to perform the selection process. Processing unit second portion 130b also communicates with controlled device CPU 305, such as to control a cursor, joystick, keyboard or other function of CPU 305. Processing unit second portion 130b further communicates with processing unit third portion 130c. Processing unit third portion 130c provides additional signal processing functions, as have been described above, to control wheelchair 310. An additional processing unit discrete component, processing unit fourth portion 130d, is included to perform additional processing of the multicellular signals and/or derivatives of these processed signals and/or processing of additional information, such collective processing used to control one or more additional controlled devices of the present invention, not shown. System 100 of FIG. 5 utilizes selector module 400 to select one or more of CPU 305, wheelchair 310 or another controlled device to be controlled by the processed signals produced by the processing unit of the present invention. In system 100 of FIG. 5, one set of processed signals emanate from one portion of the processing unit, processing unit second portion 130b, and a different set of processed signals emanate from a different portion of the processing unit, processing unit third portion 130c.

The various components of system 100 communicate with wireless transmission means, however it should be appreciated that physical cables can be used to transfer data alternatively or in addition to wireless means. These physical cables may include electrical wires, optical fibers, sound wave guide conduits, and other physical means of transmitting data and/or power and any combination of those means.

Referring back to FIG. 5, a qualified individual, operator 110 in cooperation with patient 500, is performing a patient training routine, one of numerous configuration programs or routines of the system. In an alternative embodiment, patient 500 is the operator of the patient training routine or other configuration routine. The patient training routine is shown being performed with controlled device 305. Displayed on monitor 302 is planned trajectory 711, system controlled target 712 and patient controlled object 713. In the performance of the patient training routine, multiple time varying stimulus, such as a moving system controlled target 712 are provided to the patient such that the patient can imagine moving that target, and a set of multicellular signal data can be collected by the processing unit to produce one or more algorithms to produce the processed signals of the present invention. In a preferred embodiment, after a first set of multicellular signal data is collected, and a first transfer function for producing processed signals is developed, a second set of time varying stimulus is provided in combination with a patient controlled object, such as patient controlled object 713. During the time that the patient tries to mimic the motion of the system controlled target 712 with the visual feedback of the patient controlled target 713, and a second set of multicellular signal data is collected and a second, improved transfer function is produced by the system. Additional forms of feedback can be provided to the patient, such as tactile transducer 701 shown attached to patient 500's neck, and speaker 702 shown attached to processing unit third portion 130c fixedly mounted to the back of controlled wheelchair 310. Speaker 702 and tactile transducer 701 can provide feedback in the form of a time varying stimulus, a derivative of the multicellular signals, and/or a representation of the processed signals as controlled by patient 500

In a preferred embodiment, one or more system configuration routines can be performed without an operator, with the patient as the operator, or with an operator at a remote location such as when the system of the present invention is electronically connected with a computer or computer network such as the Internet. In another preferred embodiment, the patient training routine must be performed at least one time during the use of the system, preferably before patient 500 is given, by the system, full control of one or more controlled devices. For example, limited control of CPU 305 may include the ability to send and receive email but not the ability to adjust a computer-controlled thermostat. Limited control of wheelchair 310 may be to turn left or right, but not move forward or back, or to only allow travel at a limited velocity. For the purposes of this specification, limited control may also include no control of one or more controlled devices. Each controlled device will have different parameters limited by system 100 when patient 500 has not been given full control. In a preferred embodiment, the selection of these parameters; the values to be limited; the criteria for achieving full control such as the value of a success threshold achieved during a system configuration routine such as a patient training routine; and combinations of these, are modified only in a secured way such as only by a clinician utilizing electronic or mechanical keys or passwords.

In addition to successful completion of the patient training routine, completion of one or more other configuration routines may be required for patient 500 to have full control of one or more controlled devices, or multiple successful completions of a single routine. Success is preferably measured through the measurement of one or more performance parameters during or after the configuration routine. Success will be achieved by a performance parameter being above a threshold value, such as a threshold adjustable only by a clinician, such as a clinician at a remote site utilizing a password, a user identification, an electronic ID and/or a mechanical key. These configuration routines are utilized by the system to not only determine the applicability of full control to the patient, but to set or reset one or more system configuration parameters. System configuration parameters include but are not limited to: selection of cellular signals for processing by the processing unit; criteria for the selection of cells for processing; a coefficient of a signal processing function such as amplification, filtering, sorting, conditioning, translating, interpreting, encoding, decoding, combining, extracting, sampling, multiplexing, analog to digital converting, digital to analog converting, mathematically transforming; a control signal transfer function parameter such as a transfer function coefficient, algorithm, methodology, mathematical equation, a calibration parameter such as calibration frequency; a controlled device parameter such as a controlled device boundary limit; acceptable frequency range of cellular activity; selection of electrodes to include; selection of cellular signals to include; type of frequency analysis such as power spectral density; instruction information to patient such as imagined movement type or other imagined movement instruction; type, mode or configuration of feedback during provision of processed signals to patient; calibration parameter such as calibration duration and calibration frequency; controlled device parameter such as controlled device mode; alarm or alert threshold; and a success threshold.

As depicted in FIG. 5, operator 110 utilizes configuration apparatus 120 which includes two monitors, first configuration monitor 122a and second configuration monitor 122b, configuration keyboard 123, and configuration CPU 125, to perform a calibration routine or other system configuration process such as a patient training routine, algorithm and algorithm parameter selection and output device setup. The configuration routines, such as the patient training routine, include software programs and hardware required to perform the configuration. The embedded software and/or hardware may be included in the processing unit, such as processing unit second portion 130b, be included in selector module 400, be incorporated into configuration apparatus 120, a controlled device, or combinations of these. Configuration apparatus 120 may include additional input devices, such as a mouse or joystick, or an input device for a patient with limited motion, such as a tongue switch; a tongue palate switch; a chin joystick; a Sip n' Puff joystick controller; an eye tracker device; a head tracker device; an EMG switch such as an eyebrow EMG switch; an EEG activated switch; and a speech recognition device, all not shown.

Configuration apparatus 120 may include various elements, functions and data including but not limited to: memory storage for future recall of configuration activities, operator qualification routines, standard human data, standard synthesized or artificial data, neuron spike discrimination software, operator security and access control, controlled device data, wireless communication means, remote (such as via the Internet) configuration communication means and other elements, functions and data used to provide an effective and efficient configuration on a broad base of applicable patients and a broad base of applicable controlled devices. A system electronic ID can be embedded in one or more of the discrete components at the time, including an ID embedded at the time of system configuration. In an alternative embodiment, all or part of the functionality of configuration apparatus 120 is integrated into selector module 400 such that system 100 can perform one or more configuration processes such as a calibration procedure or patient training routine, utilizing selector module 400 without the availability of configuration apparatus 120.

In order to change a system configuration parameter, system 100 includes a permission routine, such as an embedded software routine or software driven interface that allows the operator to view information and enter data into one or more components of system 100. The data entered must signify an approval of the parameter modification in order for the modification to take place. Alternatively, the permission routine may be partially or fully located in a separate device such as configuration apparatus 120 of FIG. 5, or a remote computer such as a computer that accesses system 100 via the Internet or utilizing wireless technologies. In order to access the permission routine, and/or approve the modification of the system configuration parameters, a password or security key, mechanical, electrical, electromechanical or software based, may be required of the operator. Multiple operators may be needed or required to approve a parameter modification. Each specific operator or operator type may be limited by system 100, via passwords and other control configurations, to approve the modification of only a portion of the total set of modifiable parameters of the system. Additionally or alternatively, a specific operator or operator type may be limited to only approve a modification to a parameter within a specific range of values, such as a range of values set by a clinician when the operator is a family member. Operator or operator types, hereinafter operator, include but are not limited to: a clinician, primary care clinician, surgeon, hospital technician, system 100 supplier or manufacturer technician, computer technician, family member, immediate family member, caregiver and patient.

In a preferred embodiment, the system 100 of FIG. 5 includes an interrogation function, which interrogates the system to retrieve certain information such as on the demand of an operator. Based on the analysis of the information, a recommendation for a parameter value change can be made available to the operator, such as by automatic configuration or calibration routines that are initiated by the operator initiated interrogation function. After viewing the modification, the appropriate operator would approve the change via the permission routine, such as using a computer mouse to click "OK" on a confirmation box displayed on a display monitor, or a more sophisticated, password controlled methodology.

In a preferred embodiment, an automatic or semi-automatic configuration function or routine is embedded in system 100. This embedded configuration routine can be used in place of a configuration routine performed manually by Operator 110 as is described hereabove, or can be used in conjunction with one or more manual configurations. Automatic and/or semi-automatic configuration triggering event or causes can take many forms including but not limited to: monitoring of cellular activity, wherein the system automatically changes which particular signals are chosen to produce the processed signals; running parallel algorithms in the background of the one or more algorithms currently used to create the processed signals, and changing one or more algorithms when improved performance is identified in the background event; monitoring of one or more system functions, such as alarm or warning condition events or frequency of events, wherein the automated system shuts down one or more functions and/or improves performance by changing a relevant variable; and other methods that monitor one or more pieces of system data, identify an issue or potential improvement, and determine new parameters that would reduce the issue or achieve an improvement. In a preferred embodiment of the disclosed invention, when specific system configuration parameters are identified, by an automated or semi-automated calibration or other configuration routine, to be modified for the reasons described above, an integral permission routine of the system requires approval of a specific operator when one or more of the system configuration parameters are modified.

Operator 110 may be a clinician, technician, caregiver, patient family member or even the patient themselves in some circumstances. Multiple operators may be needed or required to perform a configuration routine or approve a modification of a system configuration parameter, and each operator may be limited by system 100, via passwords and other control configurations, to only perform or access specific functions. For example, only the clinician may be able to change specific critical parameters, or set upper and lower limits on other parameters, while a caregiver, or the patient, may not be able to access those portions of the configuration procedure or the permission procedure. The configuration routine includes the setting of numerous parameters needed by system 100 to properly control one or more controlled devices. The parameters include but are not limited to various signal conditioning parameters as well as selection and de-selection of specific multicellular signals for processing to generate the device control creating a subset of signals received from the sensor to be processed. The various signal conditioning parameters include, but are not limited to, threshold levels for amplitude sorting, other sorting and pattern recognition parameters, amplification parameters, filter parameters, signal conditioning parameters, signal translating parameters, signal interpreting parameters, signal encoding and decoding parameters, signal combining parameters, signal extracting parameters, mathematical parameters including transformation coefficients and other signal processing parameters used to generate a control signal for transmission to a controlled device.

The configuration routine will result in the setting of various system configuration output parameters, all such parameters to be considered system configuration parameters of the system of the present invention. Configuration output parameters may consist of but are not limited to: electrode selection, cellular signal selection, neuron spike selection, electrocorticogram signal selection, local field potential signal selection, electroencephalogram signal selection, sampling rate by signal, sampling rate by group of signals, amplification by signal, amplification by group of signals, filter parameters by signal and filter parameters by group of signals. In a preferred embodiment, the configuration output parameters are stored in memory in one or more discrete components, and the parameters are linked to the system's unique electronic ID.

Calibration, patient training, and other configuration routines, including manual, automatic and semi-automatic routines, may be performed on a periodic basis, and may include the selection and deselection of specific cellular signals over time. The initial configuration routine may include initial values, or starting points, for one or more of the configuration output parameters. Setting initial values of specific parameters, may invoke a permission routine. Subsequent configuration routines may involve utilizing previous configuration output parameters that have been stored in a memory storage element of system 100. Subsequent configuration routines may be shorter in duration than an initial configuration and may require less patient involvement. Subsequent configuration routine results may be compared to previous configuration results, and system 100 may require a repeat of configuration if certain comparative performance is not achieved.

The configuration routine may include the steps of (a) setting a preliminary set of configuration output parameters; (b) generating processed signals to control the controlled device; (c) measuring the performance of the controlled device control; and (d) modifying the configuration output parameters. The configuration routine may further include the steps of repeating steps (b) through (d). The configuration routine may also require invoking a permission routine.

In the performance of a configuration routine, the operator 110 may involve patient 500 or perform steps that do not involve the patient. In the patient training routine and other routines, the operator 110 may have patient 500 imagine one or more particular movements, imagined states, or other imagined events, such as a memory, an emotion, the thought of being hot or cold, or other imagined event not necessarily associated with movement. The patient participation may include the patient training routine providing one or more time varying stimulus, such as audio cues, visual cues, olfactory cues, gustatory cues, tactile cues, moving objects on a display such as a computer screen, moving mechanical devices such as a robotic arm or a prosthetic limb, moving a part of the patient's body such as with an exoskeleton or FES implant, changing audio signals, changing electrical stimulation such as cortical stimulation, moving a vehicle such as a wheelchair or car; moving a model of a vehicle; moving a transportation device; and other sensory stimulus. The imagined movements may include the imagined movement of a part of the body, such as a limb, arm, wrist, finger, shoulder, neck, leg, angle, and toe, as well as imagining moving to a location, moving in a direction and moving at a velocity or acceleration.

Referring back to FIG. 5, the patient imagines moving system controlled target 712 along planned trajectory 711, as target 712 is moving as controlled by the system or manually by an operator. The current processed signal, hereinafter a representation of the processed signal, available by applying a transfer function to the multicellular signals detected during the imagined movement or other step of the patient training routine, is displayed in the form of control of patient controlled target 713. The transfer function is preferably based on multicellular signals stored during a previous imagined movement, or multiple previous imagined movements, preferably two or more sets of states of time varying stimulus. The representation of the processed signals may mimic the time varying stimulus, similar to patient controlled object 713 being a similar form to system controlled object 712. Alternatively, the time varying stimulus and representation of the processed signals may take different forms, such as a time varying stimulus consisting of an object on a visual display, wherein the representation is a moving mechanical structure, or the stimulus being a moving mechanical structure and the representation consisting of an object on a visual display. The representation of the processed signals can be provided to the patient in visual form such as a visual representation of limb motion displayed on a computer monitor, or in one or more sensory forms such as auditory, olfactory, gustatory, and electrical stimulation such as cortical stimulation. The representation of the processed signals can be provided in combinations of these and other forms.

In a preferred embodiment, the first patient training step does not include patient controlled object 713 or it includes a patient controlled target whose processed signals are not based on a set of multicellular signals collected during a previous imagined movement. Multiple steps of providing a set of states of the time varying stimulus and recording the multicellular signal data may involve different subsets of cells from which the multicellular signals are detected. Also, different sets of states of time varying stimulus may have different numbers of cells in each. Alternative to the system controlled target 712 along planned trajectory 711, the patient may imagine movements while viewing a time varying stimulus consisting of a video or animation of a person performing the specific movement pattern. In a preferred embodiment, this visual feedback is shown from the patient's perspective, such as a video taken from the person performing the motion's own eye level and directional view. Multiple motion patterns and multiple corresponding videos may be available to improve or otherwise enhance the patient training process. The patient training routine temporally correlates a set of states of the time varying stimulus with the set of multicellular signal signals captured and stored during that time period, such that a transfer function can be developed for future training or controlled device control. Correlations can be based on numerous variables of the motion including but not limited to: position, velocity and acceleration of the time varying stimulus; a patient physiologic parameter such as heart rate; a controlled device parameter; a system environment parameter; a password controlled parameter; a clinician controlled parameter; and a patient training routine parameter. In the patient training routine of FIG. 5, the controlled device, CPU 305 and controlled monitor 302 are used in the patient training routine to display the time varying stimulus as well as the representation of the processed signal. In a subsequent step, wheelchair 310 can also be employed, such as by a system controlling the wheelchair while the patient imagines the control, the wheelchair movement being the time varying stimulus.

During the time period that a set of states of the time varying stimulus is applied, multicellular signal data detected by the implanted sensor is stored and temporally correlated to that set of states of the time varying stimulus provided to the patient. In a preferred embodiment, the system of the present invention includes a second patient training routine and a second controlled device, wherein the first patient training routine is used to configure the first controlled device and the second patient training routine is used to configure the second controlled device. The two patient training routines may include different time varying stimulus, chosen to optimize the routine for the specific controlled device, such as a moving cursor for a computer mouse control system, and a computer simulated prosthetic limb for a prosthetic limb control system. In a preferred system, the first controlled device is a prosthetic arm and the second controlled device is a prosthetic leg, this system having two different time varying stimulus in the two corresponding patient training routines. In another preferred system, the first controlled device is a prosthetic arm and the second controlled device is a wheelchair, this system also having two different time varying stimulus in the two corresponding patient training routines. In an alternative, preferred embodiment, a controlled device surrogate is utilized in the patient training routine. The controlled device surrogate preferably has a larger value of one or more of: degrees of freedom; resolution; modes; discrete states; functions; and boundary conditions. Numerous boundary conditions with greater values for the surrogate device can be employed, such boundary conditions as: maximum distance; maximum velocity; maximum acceleration; maximum force; maximum torque; rotation; and position. The surrogate device employing larger values of these parameters creates the scenario wherein the patient is trained and/or tested with a device of more complexity than the eventual controlled device to be used.

The time varying stimulus may be supplied to the patient in numerous forms such as visual, tactile, olfactory, gustatory, and electrical stimulation such as cortical stimulation. The time varying stimulus may be moved around manually, automatically produced and controlled by a component of the system such as the processing unit, or produced by a separate device. The time varying stimulus may include continuous or semi-continuous motion of an object, such as an object moving on a visual display, a mechanical object moving in space, or a part of the patient's body moving in space. The time varying stimulus may be of a short duration, such as an object appearing and disappearing quickly on a display, or a flash of light.

In a preferred embodiment, the patient training routine includes multiple forms of feedback, in addition to the time varying stimulus, such feedback provided to the patient in one or more forms including but not limited to: visual; tactile; auditory; olfactory; gustatory; and electrical stimulation. The additional feedback may be a derivative of the multicellular signals, such as visual or audio feedback of one or more neuron spike modulation rates. Different forms of feedback may be provided as based on a particular device to be controlled by the processed signals. Numerous parameters for the time varying stimulus and other feedback may be adjustable, such as by the operator or patient, these parameters including but not limited to: sound volume and frequency; display brightness, contrast, size and resolution; display object size; electrical current parameter such as current or voltage; mechanical or visual object size, color, configuration, velocity or acceleration; and combinations of these.

A configuration routine such as a calibration or patient training routine will utilize one or more configuration input parameters to determine one or more system output parameters used to develop a processed signal transfer function. In addition to the multicellular signals themselves, system or controlled device performance criteria can be utilized. Other configuration input parameters include various properties associated with the multicellular signals including one or more of: signal to noise ratio, frequency of signal, amplitude of signal, neuron firing rate, average neuron firing rate, standard deviation in neuron firing rate, modulation of neuron firing rate as well as a mathematical analysis of any signal property including but not limited to modulation of any signal property. Additional configuration input parameters include but are not limited to: system performance criteria, controlled device electrical time constants, controlled device mechanical time constants, other controlled device criteria, types of electrodes, number of electrodes, patient activity during configuration, target number of signals required, patient disease state, patient condition, patient age and other patient parameters and event based (such as a patient imagined movement event) variations in signal properties including neuron firing rate activity. In a preferred embodiment, one or more configuration input parameters are stored in memory and linked to the embedded, specific, unique electronic identifier. All configuration input parameters shall be considered a system configuration parameter of the system of the present invention.

It may be desirous for the configuration routine to exclude one or more multicellular signals based on a desire to avoid signals that respond to certain patient active functions, such as non-paralyzed functions, or even certain imagined states. The configuration routine may include having the patient imagine a particular movement or state, and based on sufficient signal activity such as firing rate or modulation of firing rate, exclude that signal from the signal processing based on that particular undesired imagined movement or imagined state. Alternatively real movement accomplished by the patient may also be utilized to exclude certain multicellular signals emanating from specific electrodes of the sensor. In a preferred embodiment, an automated or semi-automated calibration or other configuration routine may include through addition, or exclude through deletion, a signal based on insufficient activity during known patient movements.

The configuration routines of the system of the present invention, such as a patient training routine in which a time varying stimulus is provided to the patient, may conduct adaptive processing, such as adapting between uses or within a single patient training routine. The adaptation may be caused by a superior or inadequate level of performance, as compared to a threshold value, such as an adjustable threshold. In a preferred embodiment, performance during a patient training routine above a threshold value causes the duration of the routine to decrease, and performance below a threshold value causes the duration of the routine to increase. Control of the controlled device or surrogate controlled device is a preferred way of measuring performance. Alternatively, a change in multicellular signals, such as a change in modulation rate may cause an adaptation to occur. A monitored difference is a first patient training event and a second patient training event, such as a difference in signal modulation, may cause an adaptation in the patient training routine, such as to preferentially choose one time varying stimulus over another time varying stimulus. Other causes include a change to a patient parameter, such as the level of patience consciousness. In a preferred embodiment, at a low level of consciousness, the patient training routine changes or discontinues. The level of consciousness may be determined by the multicellular signals detected by the sensor. Alternatively, the level of consciousness can be detected utilizing a separate sensor, such as a sensor to detect EEG or LFP signals. The patient training routine may automatically adapt, such as due to a calculation performed by the processing unit, or may adapt due to operator input.

The systems of the present invention, such as system 100 of FIG. 5, include a processing unit that processes multicellular signals received from patient 500. Processing unit second portion 130*b* and other processing unit components, singly or in combination, perform one or more functions. The functions performed by the processing unit include but are not limited to: producing the processed signals; transferring data to a separate device; receiving data from a separate device; producing processed signals for a second controlled device; activating an alarm, alert or warning; shutting down a part of or the entire system; ceasing control of a controlled device; storing data and performing a configuration.

In order for the processing unit of system 100 to perform one or more functions, one or more system configuration parameters are utilized. These parameters include pieces of data stored in, sent to, or received from, any component of system 100, including but not limited to: the sensor; a processing unit component; processing unit second portion 130*b*; or a controlled device. Parameters can be received from devices outside of system 100 as well, such as configuration apparatus 120, a separate medical therapeutic or diagnostic device, a separate Internet based device or a separate wireless device. These parameters can be numeric or alphanumeric data, and can change over time, either automatically or through an operator involved configuration or other procedure.

The processing unit, or other component of system 100 may produce multiple processed signals for controlling one or more controlled device. This second processed signals may be based on multicellular signals of the sensor, such as the same set of cells as the first processed signals are based on, or a different set of cells emanating signals. The signal processing used to produce the additional processed signals can be the same as the first, or utilize different processing, such as different transfer functions. Transfer functions may include different algorithms, coefficients such as scaling factors, different types of feedback, and other transfer function variations. Alternatively, the additional processed signals may be based on signals not received from the sensor in which the first processed signals are derived. An additional sensor, such as a similar or dissimilar sensor, may provide the signals to produce the additional processed signals, or the system may receive a signal from an included input device such as a tongue switch; tongue palate switch; chin joystick; Sip n' Puff joystick controller; eye gaze tracker; head tracker; EMG switch such as eyebrow EMG switch; EEG activated switch; speech recognition device; and any combination thereof. The additional processed signals may be derived from a monitored biological signal such as a signal based on eye motion; eyelid motion; facial muscle activation or other electromyographic activity; heart rate; EEG; LFP; respiration; and any combination thereof. In creating the additional processed signals, the processing unit may convert these alternative input signals into a digital signal, such as a digital signal used to change the state of the system, such as a change in state of an integrated configuration routine.

Figure 6:
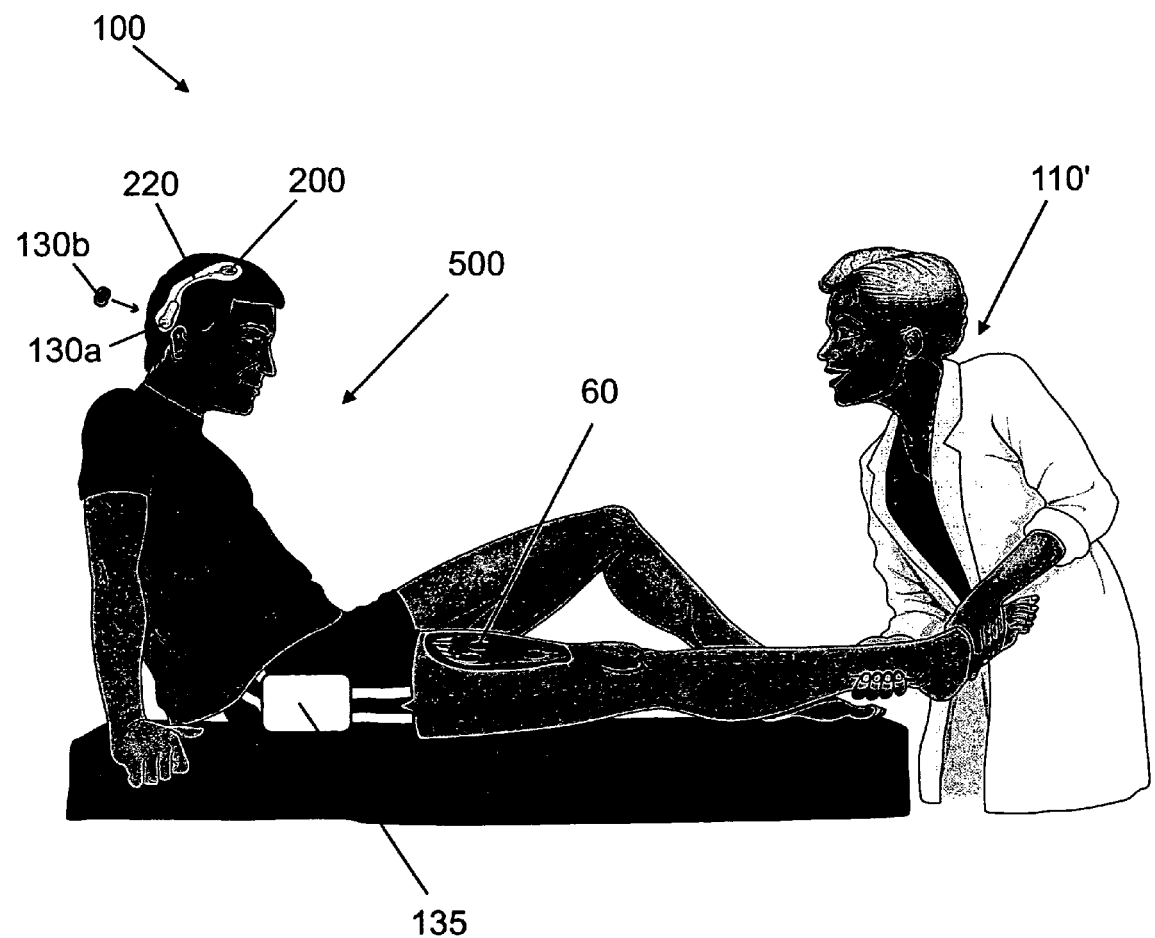
FIG. 6 illustrates another patient training apparatus of an exemplary embodiment of the biological interface apparatus, consistent with the present invention.

Referring now to FIG. 6, another preferred embodiment of the patient training apparatus of the present invention is illustrated in which the patient training apparatus consists of an implanted FES system. The controlled device of the biological interface system may be the FES system, or the FES system may be used as a patient training apparatus for a different controlled device such as a computer or a vehicle. Biological interface apparatus 100, which is described in detail in reference to FIG. 4 and FIG. 5 hereabove, includes sensor 200 and a processing unit for processing the multicellular signals that are detected by sensor 200. The processing unit comprises two discrete components, processing unit first portion 130*a* that is implanted under the scalp of patient 500, and processing unit second portion 130*b* that is external to the patient. Sensor 200 is illustrated through a view of the skull that has been cutaway, sensor 200 being implanted in the motor cortex of patient 500's brain. In a preferred embodiment, sensor 200 is implanted in a portion of the motor cortex associated one or more the joints or surrogate, prosthetic joints controlled by one or more joint movement devices of apparatus 100. In a preferred embodiment, a functional MRI (fMRI) is performed prior to the surgery in which the patient imagines moving one or more target joints, and sensor 200 is located based on information output from the fMRI. A wire bundle 220 connects sensor 200 to processing unit first portion 130*a*, which has been placed in a recess, surgically created in patient 500's skull, viewed in FIG. 1 through a cutaway of patient 500's scalp. Wire bundle 220 includes multiple, flexible insulated wires, preferably a single wire for each electrode. In an alternative embodiment, one or more single wires carry cellular signal transmissions from two or more electrodes. The surgical procedure required for the implantation of wire bundle 220, as well as sensor 200 and processing unit first portion 130a, is described in detail in reference to FIG. 4 hereabove. Alternatively or additionally, a cellular signal sensor component may be placed in numerous locations such as the spinal cord or a peripheral nerve.

Processing unit first portion 130a transmits data, such as with RF or infrared transmission means, to a receiver of processing unit second portion 130b, which is shown as in the process of being removably placed at a location near the implant site of processing unit first portion 130a. In a preferred embodiment, magnets integral to either or both processing unit discrete components are used to maintain the components in appropriate proximity and alignment to assure accurate transmissions of data. One or more patient input devices, not shown, may be affixed to patient 500. These switches are used to provide a patient activated input signal to biological interface apparatus 100. In an alternative or additional embodiment, one or more of these switches is used to provide a patient activated input to one or more components of apparatus 100. Patient input switches incorporated into one or more apparatus, device, methods and systems of the present invention can be used in the performance of various system functions or routines and/or to initiate various system functions or routines. In a preferred embodiment, a patient input switch is used to change the state of the system, such as when the system state changes to: a reset state; the next step of a configuration routine, a stopped state; an alarm state; a message sending state, a limited control of controlled device state; and any combination thereof. Alternative to the patient input switch is a monitored biological signal that is used for a similar change of state function. Applicable monitored biological signals are selected from the group consisting of: eye motion; eyelid motion; facial muscle activation or other electromyographic activity; heart rate; EEG; LFP; respiration; and any combination thereof.

Patient 500 is a patient with limited motor function such as a paraplegic or quadriplegic. Patient 500 may be an ALS patient whose motor function is deteriorating and has received biological interface apparatus 100 prior to the motor impairment reaching a severe level. Patient 500 of FIG. 6 has received an FES device including FES stimulators 60, some of which are shown in a partial cutaway view of patient 500's right thigh muscles. FES stimulators are implanted in all muscles in which motor function is to be restored, such as in a majority of leg muscles for a paraplegic patient. Interface 135, shown attached near the patient's hip, includes a power supply, such as a rechargeable or replaceable battery, and may supply power to one or more components of apparatus 100. Interface 135 includes wireless transmission and receiving means, such as an RF transceiver, and can send and receive information to or from each FES stimulator, as well as processing unit second portion 130b. Interface 135 further includes multiple electronic components to perform mathematical computations or other signal processing functions, as well as provide memory storage. Interface 135 may provide a function of further processing the multicellular signals or a derivative of the multicellular signals.

To conduct the patient training routine of the present invention, the FES device stimulators, such as stimulators 60, receive signals not from the multicellular signals of sensor 200, but from the system via the patient training routine and the patient training signal, that cause contractions of one or more muscles of patient 500 such that one or more limbs of patient 500 are moved. This limb movement provides the time varying stimulus for the patient imagined movements such that multicellular signals can be stored and correlated to one or more sets of other data, such as a temporal correlation to the patient training signal, a derivative of the patient training signal, or a set of data that represents the actual movement of the one or more patient limbs, such as a data set resulting from image processing of a video of the time varying stimulus movement.

In a preferred embodiment, the processed signals transmitted by processing unit second portion 130b are transmitted to the multiple FES stimulators 60, such as by way of interface 135, to cause muscle contractions such as those used to walk or change from a sitting to a standing position, such that the FES device is not only the patient training apparatus of the present invention but also a controlled device of the present invention. In order for apparatus 100 to perform in a safe and reliable manner, one or more configuration routines, such as a calibration routine and the patient training routine described above, and stored in electronic memory of the processing unit, will be performed. The configuration routine may require the use of an operator, not the patient, such as physical therapist 110' of FIG. 6. The patient training or other configuration routine, may involve configuration of the joint movement device, such as an exercise to determine patient range of motion. In a preferred embodiment, physical therapist 110' records numerous parameters associated with acceptable patient movements, as well as angles, positions, forces and other factors to avoid. Physical therapist 110' takes the information and manually enters this data such as by way of a configuration apparatus, as has been described in detail in reference to FIG. 5, which transmits the data to processing unit second portion 130b and/or interface 135.

In another preferred embodiment, apparatus 100 includes one or more integral physical therapy routines, such as routine that systematically increases a patient range. Information stored during each physical therapy event is captured either automatically, or manually as entered by physical therapist 110'. In another preferred embodiment, apparatus 100 includes one or more sensors, not shown, such as sensors whose signals are received by interface 135 and/or processing unit second portion 130b. An EMG sensor can be used to indicate a level of spasticity and/or a level of reflexivity used by apparatus 100 to improve a physical therapy event. A pressure sensor, force sensor or strain sensor may produce a signal that is compared to a threshold used to limit the processed signals to one or more minimums or maximums for values of controlled device performance.

Sensors may be used to monitor resistance to movement or amount of force required to perform a task. Physiologic sensors can be included such as a sensor selected from the group consisting of: EKG; respiration; blood glucose; temperature; blood pressure; EEG; perspiration; and combinations of the preceding. Output of the physiologic sensor can be used by the processing unit or a separate computational component of apparatus 100 to maintain the physical therapy within a range of values, avoid patient discomfort or potential adverse event. These systems may have one or more thresholds, such as adjustable thresholds, to detect irregular heart rate, nausea, pain, rise in blood pressure, and other adverse conditions. Physiologic data, as well as other recorded data can be stored and statistically trended between physical therapy events, again to optimize the therapy and/or avoid complications.

Numerous methods are provided in the multiple embodiments of the disclosed invention. A preferred method embodiment includes providing a patient training routine for a biological interface apparatus that must be performed by an operator. The biological interface system is for collecting multicellular signals emanating from one or more living cells of a patient and for transmitting processed signals to control a device. The biological interface system comprises: a sensor for detecting the multicellular signals, the sensor consisting of a plurality of electrodes to allow for detection of the multicellular signals; a processing unit for receiving the multicellular signals from the sensor, for processing the multicellular signals to produce processed signals, and for transmitting the processed signals; a controlled device for receiving the processed signals; and a patient training routine for generating one or more system configuration parameters.

It should be understood that numerous other configurations of the systems, devices and methods described herein could be employed without departing from the spirit or scope of this application. It should be understood that the system includes multiple functional components, such as a sensor for detecting multicellular signals, a processing unit for processing the multicellular signals to produce processed signals, and the controlled device that is controlled by the processed signals. Different from the logical components are physical or discrete components, which may include a portion of a logical component, an entire logical component and combinations of portions of logical components and entire logical components. These discrete components may communicate or transfer information to or from each other, or communicate with devices outside the system. In each system, physical wires, such as electrical wires or optical fibers, can be used to transfer information between discrete components, or wireless communication means can be utilized. Each physical cable can be permanently attached to a discrete component, or can include attachment means to allow attachment and potentially allow, but not necessarily permit, detachment. Physical cables can be permanently attached at one end, and include attachment means at the other.

The sensors of the systems of this application can take various forms, including multiple discrete component forms, such as multiple penetrating arrays that can be placed at different locations within the body of a patient. The processing unit of the systems of this application can also be contained in a single discrete component or multiple discrete components, such as a system with one portion of the processing unit implanted in the patient, and a separate portion of the processing unit external to the body of the patient. The sensors and other system components may be utilized for short term applications, such as applications less than twenty four hours, sub-chronic applications such as applications less than thirty days, and chronic applications. Processing units may include various signal conditioning elements such as amplifiers, filters, signal multiplexing circuitry, signal transformation circuitry and numerous other signal processing elements. In a preferred embodiment, an integrated spike sorting function is included. The processing units performs various signal processing functions including but not limited to: amplification, filtering, sorting, conditioning, translating, interpreting, encoding, decoding, combining, extracting, sampling, multiplexing, analog to digital converting, digital to analog converting, mathematically transforming and/or otherwise processing cellular signals to generate a control signal for transmission to a controllable device. The processing unit utilizes numerous algorithms, mathematical methods and software techniques to create the desired control signal. The processing unit may utilize neural net software routines to map cellular signals into desired device control signals. Individual cellular signals may be assigned to a specific use in the system. The specific use may be determined by having the patient attempt an imagined movement or other imagined state. For most applications, it is preferred that that the cellular signals be under the voluntary control of the patient. The processing unit may mathematically combine various cellular signals to create processed signals for device control.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A biological interface system comprising:
   a sensor comprising a plurality of electrodes for detecting multicellular signals emanating from living cells of a patient;
   a processing unit configured to receive the multicellular signals from the sensor;
   a patient training apparatus configured to controllably move one or more joints of the patient in response to a patient training signal provided by the processing unit,
   wherein the processing unit is configured to perform an integrated patient training routine including:
     providing a time varying stimulus to the patient in the form of a patient training signal,
     storing a set of multicellular signal data detected during movement of the one or more joints by the patient training apparatus and detected while providing a set of states of the time varying stimulus, and
     correlating the set of multicellular signal data to a second set of data related to the movement of the one or more joints, and
   wherein, after completion of the patient training routine, the processing unit is configured to process multicellular signals from the sensor to produce a processed signal for control of a controlled device, the processing based, at least in part, on the correlation of the set of multicellular signal data, stored during the patient training routine, and the second set of data.

2. The system of claim 1, wherein the patient training signal is initiated by an operator.

3. The system of claim 2, wherein the operator comprises the patient.

4. The system of claim 3, wherein the patient training signal is initiated by the patient by activating one or more of: chin joystick; eyebrow EMG switch; EEG activated switch; eye tracker; head tracker; neck movement switch; shoulder movement switch; sip-n-puff joystick controller; speech recognition switch; tongue switch; and any combination thereof.

5. The system of claim 1, wherein the patient training signal is provided manually by the operator.

6. The system of claim 5, wherein the operator comprises the patient's clinician.

7. The system of claim 1, wherein the patient training signal is configured to be modified by an operator.

8. The system of claim 7, further comprising a user interface, wherein the patient training routine is configured by the operator utilizing the user interface.

9. The system of claim 1, further comprising a configuration apparatus, wherein the configuration apparatus receives the patient training signal.

10. The system of claim 1, wherein the sensor is adapted to be placed in a portion of the motor cortex associated with a specific limb, and the one or more joints moved comprise a part of the specific limb.

11. The system of claim 10, wherein the sensor is adapted to be placed in an arm-hand portion of the motor cortex.

12. The system of claim 1, wherein the patient training apparatus is used for patient training only.

13. The system of claim 1, wherein the patient training apparatus comprises an exoskeleton device.

14. The system of claim 13, wherein the exoskeleton device comprises also the controlled device.

15. The system of claim 1, wherein the patient training apparatus comprises an Functional Electrical Stimulation (FES) device.

16. The system of claim 15, wherein the FES device comprises the controlled device.

17. The system of claim 1, wherein the patient training apparatus comprises a robotic arm that is adapted to be attached to a limb or digit of the patient.

18. The system of claim 1, wherein the patient training apparatus is configured to move a joint of the patient's arm.

19. The system of claim 1, wherein the patient training apparatus is configured to move a joint of the patient's leg.

20. The system of claim 1, wherein the patient training apparatus is configured to move a joint of a digit of the patient.

21. The system of claim 1, wherein the patient training apparatus is adapted to be attached to the patient's hand.

22. The system of claim 21, wherein the patient training signal is configured to cause the hand to move in a two dimensional plane.

23. The system of claim 21, wherein the patient training signal is configured to cause the hand to move in a three dimensional space.

24. The system of claim 1, further comprising a configuration apparatus.

25. The system of claim 24, wherein the configuration apparatus comprises the patient training apparatus.

26. The system of claim 24, wherein the configuration apparatus comprises a user interface.

27. The system of claim 1, further comprising a second patient training apparatus.

28. The system of claim 27, wherein the second patient training apparatus receives the patient training signal.

29. The system of claim 27, wherein the patient training routine provides a second patient training signal, and the second patient training apparatus receives the second patient training signal.

30. The system of claim 1, wherein the correlation through the patient training routine comprises a temporal correlation.

31. The system of claim 1, wherein the second set of data comprises a derivative of the patient training signal, and the stored multicellular signal data is temporally correlated with the patient training signal.

32. The system of claim 1, wherein the correlation through the patient training routine comprises mathematically matching two periodicities of motion.

33. The system of claim 1, wherein the correlation through the patient training routine comprises mathematically matching two periodicities of signals.

34. The system of claim 1, wherein the stored multicellular signal data is correlated with one or more of: a physiologic parameter of the patient; a controlled device parameter; a system environment parameter; a password controlled parameter; a clinician controlled parameter; and a patient training routine parameter.

35. The system of claim 1, wherein the second set of data comprises a derivative of the patient training signal.

36. The system of claim 1, wherein the second set of data comprises a derivative of a motion of the patient training apparatus.

37. The system of claim 36, wherein the motion is recorded by a second sensor in the patient training apparatus.

38. The system of claim 36, wherein the motion is recorded by a visual recording device.

39. The system of claim 38, wherein the visual recording device output is processed to create the second set of data.

40. The system of claim 1, wherein the patient training routine is used to generate one or more system configuration parameters used by the processing unit to produce the processed signal.

41. The system of claim 1, wherein less than full control of the controlled device is available to the patient prior to a successful completion of the patient training routine.

42. The system of claim 41, further comprising a threshold value to determine the successful completion.

43. The system of claim 42, wherein the threshold value is adjustable.

44. The system of claim 43, wherein the system is configured to allow a clinician to adjust the threshold value.

45. The system of claim 43, wherein the system is configured such that an adjustment to the threshold value is made from a remote location.

46. The system of claim 43, wherein the system is configured to perform a permission routine prior to an adjustment to the threshold value.

47. The system of claim 46, wherein the adjustment is controlled by one or more of: a password; a user identification; an electronic ID; and a mechanical key.

48. The system of claim 1, wherein the patient training routine utilizes the controlled device.

49. The system of claim 1, further comprising a surrogate of the controlled device for use by the patient training routine.

50. The system of claim 1, wherein the patient training routine provides feedback to the patient.

51. The system of claim 50, wherein the feedback comprises a derivative of the multicellular signals.

52. The system of claim 51, wherein the derivative comprises neural spike modulation rates.

53. The system of claim 50, wherein the feedback is provided by one or more of the following forms: auditory; olfactory; gustatory; visual; electrical stimulation; and any combination thereof.

54. The system of claim 50, wherein the feedback comprises a representation of the processed signal produced by the processing unit.

55. The system of claim 54, wherein the representation comprises one or more of the following: moving an object on screen; moving a mechanical device; moving part of the patient's body; changing an audible signal; and any combination thereof.

56. The system of claim 54, wherein the feedback further comprises a representation of a difference between desired control conditions and actual control conditions.

57. The system of claim 50, wherein the feedback comprises a modified representation of the processed signal.

58. The system of claim 57, wherein the modified representation represents an artificially improved processed signal with more accurate control.

59. The system of claim 58, wherein the artificial improvement decreases as processed signal accuracy improves.

60. The system of claim 1, wherein the patient training routine comprises a software program.

61. The system of claim 60, wherein the software program is embedded in the system.

62. The system of claim 61, wherein the software program is embedded in the processing unit.

63. The system of claim 1, further comprising a separate device in which the patient training routine is embedded.

64. The system of claim 1, wherein the patient training routine provides a predictory path or target.

65. The system of claim 64, wherein the predictory path or target comprises a visual image.

66. The system of claim 1, wherein a transfer function based on the correlated set of multicellular signals and the second set of data is used by the processing unit to create the processed signal.

67. The system of claim 66, wherein the second set of data comprises patient training signal data or a derivative of patient training signal data.

68. The system of claim 67, wherein the second set of data further comprises data from an additional source.

69. The system of claim 68, wherein the data from the additional source is correlated with the multicellular data.

70. The system of claim 1, further comprising the controlled device.

71. The system of claim 70, wherein the controlled device does not move any patient joints.

72. The system of claim 70, wherein the controlled device comprises a computer.

73. The system of claim 72, wherein the processed signal controls a computer cursor.

74. The system of claim 1, wherein the processing unit creates a transfer function to create the processed signal, the transfer function based on the set of stored multicellular signal data and the patient training signal.

75. The system of claim 1, wherein the processing unit creates a transfer function to create the processed signal, the transfer function based on the set of stored multicellular signal data and the second set of data.

76. A method of performing a patient training procedure for a biological interface system, comprising: providing the biological interface system of claim 1; and providing the patient training signal to the system, so that the patient training apparatus moves one or more joints of the patient.

77. The method of claim 76, further comprising storing the set of multicellular signal data during a movement of the patient training apparatus by the patient training signal.

78. The method of claim 77, further comprising temporally correlating the set of multicellular signal data with the patient training signal.

79. The method of claim 78, further comprising creating a transfer function with the processing unit based on the set of stored multicellular signal data and the patient training signal.

80. The method of claim 79, further comprising creating the processed signal with the processing unit by applying the transfer function to the multicellular signals received from the sensor.

81. A method of performing a patient training procedure for a biological interface system, comprising
detecting multicellular signals emanating from living cells of a patient using a sensor comprising a plurality of electrodes
a processing unit receiving the multicellular signals from the sensor and
a patient training apparatus controllably moving one or more joints of the patient in response to a patient training signal provided by the processing unit
the processing unit further performing an integrated patient training routine comprising:
providing a time varying stimulus in the form of a patient training signal,
storing a set of multicellular signal data detected during movement of the one or more joints by the patient training apparatus and detected while providing a set of states of the time varying stimulus, and
correlating the set of multicellular signal data to a second set of data related to the movement of the one or more joints, and
wherein, after completion of the patient training routine, the processing unit processes multicellular signals from the sensor to produce a processed signal for control of a controlled device, the processing based, at least in part, on the correlation of the set of multicellular signal data, stored during the patient training routine, and the second set of data.

82. The method of claim 81, wherein the patient training signal is initiated by an operator.

83. The method of claim 81, wherein the operator comprises the patient.

84. The method of claim 81, wherein the patient training signal is initiated by the patient by activating one or more of: chin joystick; eyebrow EMG switch; EEG activated switch; eye tracker; head tracker; neck movement switch; shoulder movement switch; sip-n-puff joystick controller; speech recognition switch; tongue switch; and any combination thereof.

85. The method of claim 81, wherein the sensor is placed in an arm-hand portion of the motor cortex.

86. The method of claim 81, wherein the patient training apparatus is used for patient training only.

87. The method of claim 81, wherein the patient training apparatus comprises an exoskeleton device.

88. The system of claim 87, wherein the exoskeleton device comprises also the controlled device.

89. The method of claim 81, wherein the patient training apparatus comprises an Functional Electrical Stimulation (FES) device.

90. The method of claim 89, wherein the FES device comprises the controlled device.

91. The method of claim 81, wherein the patient training apparatus comprises a robotic arm that is attached to a limb or digit of the patient.

92. The method of claim 81, wherein the patient training apparatus is configured to move a joint of the patient's arm.

93. The method of claim 81, wherein the patient training apparatus is configured to move a joint of the patient's leg.

94. The method of claim 81, wherein the patient training apparatus is configured to move a joint of a digit of the patient.

95. The method of claim 81, wherein the patient training apparatus is attached to the patient's hand.

96. The method of claim 81, wherein the patient training signal is configured to cause the hand to move in a two dimensional plane.

97. The method of claim 81, wherein the patient training signal is configured to cause the hand to move in a three dimensional space.

98. The method of claim 81, further comprising a second patient training apparatus.

99. The method of claim 98, wherein the second patient training apparatus receives the patient training signal.

100. The method of claim 98, wherein the patient training routine provides a second patient training signal, and the second patient training apparatus receives the second patient training signal.

101. The method of claim 81, wherein the patient imagines a movement during an actual movement of the one or more joints.

102. The method of claim 101, wherein the imagined movement comprises an attempt at imagining moving the joints in a similar manner to the movement caused by the patient training apparatus.

103. The method of claim 81, wherein the correlation through the patient training routine comprises a temporal correlation.

104. The method of claim 81, wherein the second set of data comprises a derivative of the patient training signal, and the stored multicellular signal data is temporally correlated with the patient training signal.

105. The method of claim 81, wherein the correlation through the patient training routine comprises mathematically matching two periodicities of motion.

106. The method of claim 81, wherein the correlation through the patient training routine comprises mathematically matching two periodicities of signals.

107. The method of claim 81, wherein the stored multicellular signal data is correlated with one or more of: a physiologic parameter of the patient; a controlled device parameter; a system environment parameter; a password controlled parameter; a clinician controlled parameter; and a patient training routine parameter.

108. The method of claim 81, wherein the second set of data comprises a derivative of the patient training signal.

109. The method of claim 81, wherein the second set of data comprises a derivative of a motion of the patient training apparatus.

110. The method of claim 109, wherein the motion is recorded by a second sensor in the patient training apparatus.

111. The method of claim 109, wherein the motion is recorded by a visual recording device.

112. The method of claim 111, wherein the visual recording device output is processed to create the second set of data.

* * * * *